United States Patent
Campbell-Tofte

(10) Patent No.: US 7,429,395 B2
(45) Date of Patent: Sep. 30, 2008

(54) **ANTI-DIABETIC EXTRACT ISOLATED FROM *RAUVOLFIA VOMITORIA* AND *CITRUS AURANTIUM*, AND METHOD OF USING SAME**

(76) Inventor: Joan Campbell-Tofte, Adolphsvej 10, DK-2820 Gentofte (DK)

( * ) Notice: Subject to any disclaimer, the term of this patent is extended or adjusted under 35 U.S.C. 154(b) by 0 days.

(21) Appl. No.: 11/260,504

(22) Filed: Oct. 26, 2005

(65) Prior Publication Data

US 2006/0115543 A1 Jun. 1, 2006

Related U.S. Application Data

(60) Provisional application No. 60/623,640, filed on Oct. 29, 2004.

(51) Int. Cl.
*A61K 36/752* (2006.01)
(52) U.S. Cl. .................................... 424/736
(58) Field of Classification Search .............. None
See application file for complete search history.

(56) References Cited

U.S. PATENT DOCUMENTS 6,147,054 A * 11/2000 De Paoli Ambrosi .......... 514/23

FOREIGN PATENT DOCUMENTS

| GB | 734108 | 7/1955 |
|----|--------|--------|
| GB | 809912 | 3/1959 |

OTHER PUBLICATIONS

1991. G. Kweifio-Okai. Antiiflammatory activity of a Ghanaian antiarthritic herbal preparation: II. Journal of Ethnopharmacology, 33 129-133.*
Written Opinion of the International Searching Authority. PCT/IB2005/004076. separate sheet. sheet 2. Apr. 2005.*
Amole et al. "Antipyretic Effect of *Rauwolfia vomitoria* in Rabbits" (1999) *Nigerian Journal of National Products & Medicine* 3:77-78.
Campbell et al. "Tissue lipid lowering-effect of a traditional Nigerian anti-diabetic infusion of *Rauwolfia vomitoria* foliage and *Citrus aurantium* fruit" (2006) *Journal of Ethnopharmacology* 104(3):379-386.
Colker et al. "Effects of *Citrus aurantium* Extract, Caffeine, and St. John's Wort on Body Fat Loss, Lipid Levels, and Mood States in Overweight Healthy Adults" (1999) *Current Therapeutic Research* 60(3):145-153.
Pernille Ditmar Andersen & Laila YDE "Examination of a plant extract from Nigerian of *Rauwolfia vomitoria* and *Citrus aurantium* traditionally used for Diabetes mellitus type II" (2002) *The Danish University of Pharmaceutical Science*, Copenhagen, Denmark—URL:http://info.dfh.dk/publikationer/annual_report_02.pdf [retrieved on May 10, 2006] "Annual Report 2002".
Preuss et al. "*Citrus aurantium* as a Thermogenic, Weight-Reduction Replacement for Ephedra: An Overview" (2002) *Journal of Medicine* 33(1-4):247-264.
International Search Report and Written Opinion re: PCT/IB2005/004076 dated Aug. 8, 2006.
Burkill, "The Useful plants of West Tropical Africa", *Apocynaceae* (1985) I:174-176.
"Pharmacological Action Of *Rauwolfia vomitoria* AFZ", *Vietnam Medicinal and Aromatic Plants Newsletter* (1991); 2:6-7.

* cited by examiner

*Primary Examiner*—Christopher R. Tate
*Assistant Examiner*—Melenie McCormick
(74) *Attorney, Agent, or Firm*—Foley & Lardner LLP; Antoinette F. Konski

(57) ABSTRACT

This invention provides a process for extracting a pharmaceutically active fraction from the foliage (leaves and stems) and/or roots of *Rauvolfia vomitoria* and the fruit of *Citrus aurantium*. In one aspect, the process requires extracting from a boiled tea of *Rauvolfia vomitoria* foliage and/or roots and *Citrus aurantium* fruit an active fraction made by filtering the boiled tea and concentrating the supernatant. In one embodiment, the fraction is concentrated by freeze drying the supernatant. The fraction is useful to treat a disorder associated with abnormally elevated glucose levels in a subject by administering to the subject a therapeutically effective amount of the extract or a pharmaceutical composition containing the extract. Such conditions include, but are not limited to the diabetes Type II, abnormal steraroyl-CoA desaturase activity, hyperphagia, abnormal lipid mobilization, abnormal fatty acid profile from the eye of the subject, ulcers and a glucosuria.

11 Claims, 10 Drawing Sheets

ANTI-DIABETIC EXTRACT ISOLATED FROM *RAUVOLFIA VOMITORIA* AND *CITRUS AURANTIUM*, AND METHOD OF USING SAME

CROSS-REFERENCE TO RELATED APPLICATIONS

This application claims priority under 35 U.S.C. § 119 (e) to U.S. Provisional Application Ser. No. 60/623,640, filed Oct. 29, 2004, the contents of which are hereby incorporated by reference into the present disclosure.

FIELD OF THE INVENTION

The present invention is in the field of pharmaceuticals. In particular, it is related to the field of anti-diabetic pharmaceuticals for the prevention and treatment of disease.

BACKGROUND

Insulin, a hormone produced by the pancreas, makes glucose available to cells in the human body for the purpose of obtaining energy. Diabetes mellitus is primarily a disturbance of the body's glucose or carbohydrate metabolism. In diabetes mellitus Type I, the pancreas produces little insulin or it does not produce it at all. Treatment requires daily insulin injections so that a diabetic can survive. In diabetes mellitus Type II, the pancreas produces insulin, but the quantity of insulin is insufficient or it is less effective due to the cellular resistance, or both. In each of these forms there are various abnormalities, but the basic defects to which these abnormalities can be attributed are: (1) the reduced entering of glucose into various "peripheral" tissues; and (2) the increased releasing of glucose from the liver into the bloodstream (increased liver glucogenesis).

The World Health Organization (WHO) has estimated that 2 to 10 out of every 100 people will develop the condition during their lifetime and that 90% of these will be of the Type II, late onset non-insulin dependent diabetes mellitus. Nathan (1993) New Eng. J. Med. 328:1676-1685. In Type II diabetes, the insulin stimulated glucose uptake and utilization in liver, skeletal muscle and adipose tissue is impaired. Zimmet (1982) Diabetologia 22:399-411. The defects can be improved by caloric restriction and exercise. In the later stages of the disease, the only recourse for patients is a life-long hypoglycemic therapy.

Currently approved treatments for Type II diabetes include the administration of sulphonamides, biguanidines (Turner and Clapham (1998) Prog. Drug. Res. 51:33-94) and thiazolidinediones. Kohlroser et al. (2000) Am. J. Gast. 96:272-276. The drawbacks of the currently available drugs include harmful side effects and numerous counter indications (e.g. impossibility of application in pregnancy and during the suckling period), as well as their ineffectiveness in stemming the tissue complications that arise from long-term Type II diabetes. Therefore, new therapies are under investigation, e.g., the administration of herbal extracts.

For example, U.S. Patent Publ. No. 20030206976 discloses an herbal extract from a composition which contains: *Centaurii umbellatum*, Gentianaceae (centaury plant), *Teraxacum officinale*, Asteraceae (dandelion root), *Juniperi communis L*, Cupresaceae (juniper berry), *Urticae dioica L*, Urticeae (nettle plant), *Urticae dioica L*, Urticaceae (nettle root), *Cichorium intybus L*, Cichoriaceae (chicory root), *Morus nigra L*, Moraceae, (mulberry leaf), *Achilleae millefolium L*, Asteraceae (yarrow flower), *Vaccinium myrtillus L*, Ericaceae (bilberry leaf), *Phaseolus vulgaris L*, Fabaceae (bean pods), *Valeriana officinalis L*, Valerlanaceae (Valerian root). The extract is used to treat diabetes mellitus Type II.

U.S. Patent Publ. No. 20030086985 discloses a process for isolating an extract from *Argyrobium roseum* that contains the flavonoid glycoside and which possesses hypoglycaemic activity. Compositions containing this extract are useful to treat various hyperglycaemic conditions including non-insulin dependent diabetes mellitus disease. U.S. Patent Publication 20020187201 discloses a process for the control of diabetes mellitus using natural products isolated from *Perna viridis*.

However, a need still exists to find a composition and treatment with long-term effects. The invention described here satisfies this need and provides related advantages as well.

DISCLOSURE OF THE INVENTION

This invention provides a process for extracting a pharmaceutically active fraction from the foliage (leaves and stems) and/or roots of *Rauvolfia vomitoria* and the fruit of *Citrus aurantium*. In one aspect, the process requires extracting from a boiled tea of *Rauvolfia vomitoria* foliage and/or roots and *Citrus aurantium* fruit an active fraction made by filtering the boiled tea and concentrating the supernatant. In one embodiment, the fraction is concentrated by freeze drying the supernatant.

Also provided by this invention is a method of treating a disorder associated with abnormally elevated glucose levels in a subject by administering to the subject a therapeutically effective amount of the extract or a pharmaceutical composition containing the extract. Such conditions include, but are not limited to the diabetes Type II, abnormal steraroyl-CoA desaturase activity, hyperphagia, abnormal lipid mobilization, abnormal fatty acid profile from the eye of the subject, ulcers and a glucosuria.

MODES FOR CARRYING OUT THE INVENTION

Figure 1:
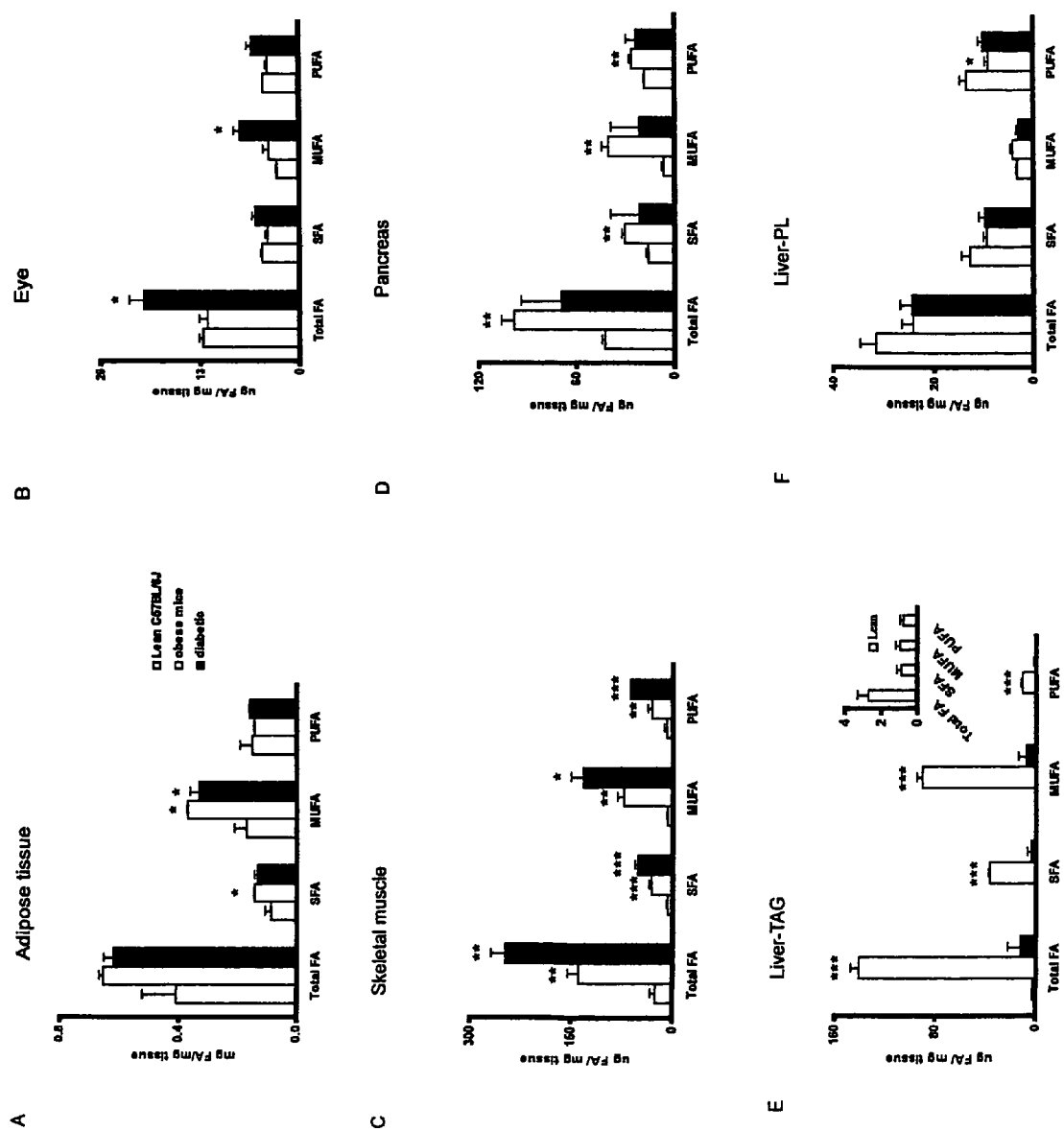
FIG. 1 compares total fatty acid (Total FA) and the different fatty acid subclass contents (saturated fatty acids, SFA; MUFA and PUFA) in adipose tissue (A), eye (B), skeletal muscle (C), pancreas (D), liver-triglyceride fraction (E) and liver-phopholipid fraction (F), respectively from lean, obese and diabetic C57BL mice. Data are expressed as mean±SEM values. Significant difference of data from obese and diabetic mice from that in the lean controls is expressed as *=$p<0.05$; =$p<0.01$; *=$p<0.001$.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of organic chemistry, analytical chemistry, biochemistry and physiology, which are within the skill of the art. Such techniques are explained fully in the literature.

Definitions

As used herein, certain terms may have the following defined meanings.

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are well known in the art.

The term "isolated" means separated from constituents, cellular and otherwise, in which the compound, composition or extract, is normally associated with in nature.

A "subject" or "host" is a vertebrate, preferably an animal or mammal, more preferably a human patient. Mammals include, but are not limited to, murines, rats, simians, human patients, farm animals, sport animals, and pets.

As used herein, to "treat" includes systemic amelioration of the symptoms associated with the pathology and/or a delay in onset of symptoms. Clinical and sub-clinical evidence of "treatment" will vary with the pathology, the individual and the treatment. For example, administration for the treatment of diabetic conditions can result in lowering blood glucose levels and cessation of glycosurea. In one aspect, "treatment" also includes "curing". Applicant shows that patients taking the extract for a period from about 30 days to about 180 days, (or alternatively from about 60 days to about 120 days) for example, often are not required to repeat the treatment. They remain symptom-free without the need for continuous treatment.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin REMINGTON'S PHARM. Sd., 15th Ed. (Mack Publ. Co., Easton (1975)).

An "effective amount" is an amount sufficient to effect beneficial or desired results. For example, a therapeutic amount is one that achieves the desired therapeutic effect. This amount may be the same or different from a prophylactically effective amount, which is an amount necessary to prevent onset of disease or disease symptoms. An effective amount can be administered in one or more administrations, applications or dosages.

"Type I diabetes mellitus" (formerly called type I, IDDM or juvenile diabetes)" is characterized by beta cell destruction caused by an autoimmune process, usually leading to absolute insulin deficiency. Report of the Expert Committee on the Diagnosis and Classification of Diabetes Mellitus. Diabetes Care (1997) 20:1183-97 (hereinafter "Expert Report (1997)). National Diabetes Data Group. Diabetes in America. 2d ed. Bethesda, Md.: National Institutes of Health, National Institute of Diabetes and Digestive and Kidney Diseases, (1995)

NIH Publication No. 95-1468 (hereinafter "NIH (1995)"). The onset is usually acute, developing over a period of a few days to weeks. Over 95 percent of persons with Type I diabetes mellitus develop the disease before the age of 25, with an equal incidence in both sexes and an increased prevalence in the white population. A family history of Type I diabetes mellitus, gluten enteropathy (celiac disease) or other endocrine disease is often found. Most of these patients have the "immune-mediated form" of Type I diabetes mellitus with islet cell antibodies and often have other autoimmune disorders such as Hashimoto's thyroiditis, Addison's disease, vitiligo or pernicious anemia. A few patients, usually those of African or Asian origin, have no antibodies but have a similar clinical presentation; consequently, they are included in this classification and their disease is called the "idiopathic form" of Type I diabetes mellitus. Expert Report (1997) and NIH (1995).

"Type 2 diabetes mellitus" (formerly called NIDDM, Type II or adult-onset) is characterized by insulin resistance in peripheral tissue and an insulin secretory defect of the beta cell. Expert Report (1997) and NIH (1995). This is the most common form of diabetes mellitus and is highly associated with a family history of diabetes, older age, obesity and lack of exercise. It is more common in women, especially women with a history of gestational diabetes, and in blacks, Hispanics and Native Americans. Insulin resistance and hyperinsulinemia eventually lead to impaired glucose tolerance. Defective beta cells become exhausted, further fueling the cycle of glucose intolerance and hyperglycemia. The etiology of Type II diabetes mellitus is multifactorial and probably genetically based, but it also has strong behavioral components.

Types of diabetes mellitus of various known etiologies are grouped together to form the classification called "other specific types." This group includes persons with genetic defects of beta-cell function (this type of diabetes was formerly called MODY or maturity-onset diabetes in youth) or with defects of insulin action; persons with diseases of the exocrine pancreas, such as pancreatitis or cystic fibrosis; persons with dysfunction associated with other endocrinopathies (e.g., acromegaly); and persons with pancreatic dysfunction caused by drugs, chemicals or infections. Expert Report (1997) and NIH (1995).

Applicant has identified a process for extracting a pharmaceutically active fraction from the foliage (leaves and stems) and/or roots of *Rauvolfia vomitoria* and the fruit of *Citrus aurantium*. In one aspect, the process requires extracting from a boiled tea of *Rauvolfia vomitoria* foliage and/or roots and *Citrus aurantium* fruit an active fraction made by filtering the boiled tea and concentrating the supernatant. In one embodiment, the fraction is concentrated by freeze drying the supernatant.

*Rauvolfia vomitoria* occurs widely in coastal and inland parts of tropical West Africa. The species is a well-known medicinal plant used by different peoples in Africa as the major or minor part of concoctions used for treating various ailments. Sofowora, Medicinal Plants and Traditional Medicine in Africa, Wiley and Sons, Chichester (1982); Burkill, The Useful Plants of Tropical West Africa, Vol. 1 (1985). *Rauvolfia vomitoria* was previously investigated for alkaloid content, especially for those with hypotensive and anti-inflammatory properties. Chatterjee & Bandyopadhyay (1979) Ind. J. Chem. 28B: 87-88; Amer & Court (1980) Phytochemistry 19: 1833-1836; Kweifio-Okai (1991) J. Ethno Pharmacology 33: 263-267. *Citrus aurantium* is reported as having a weight reduction effect when combined with a strict diet. Preuss et al. (2002) J. Med. 33:247-264. In addition, *C. aurantium* has been shown to be radioprotective because it is rich in flavonoids with anti-oxidative activity. Hosseinimehr et al. (2003) J. Rad. Res. (Tokyo) 44:237-241.

This invention provides a biologically active composition consisting essentially of a liquid extract obtained from *Rauvolfia vomitoria* and *Citrus aurantium*. In one aspect, the extract is separated from the boiled leaves and stems of *Rauvolfia vomitoria* and the boiled fruit of *Citrus aurantium*. The extract can be combined with a carrier, such as a pharmaceutically acceptable carrier. Alternatively and/or additionally, an effective amount of an agent that lowers blood glucose levels can be added to the composition.

This invention also provides a method of treating a disorder associated with abnormally elevated glucose levels in a subject by administering to the subject a therapeutically effective amount of the extract or a pharmaceutical composition containing the extract. As used in this context, to "treat" means to alleviate the symptoms associated with abnormally high levels of glucose. Such conditions include, but are not limited to the diabetes Type II, abnormal stearoyl-CoA desaturase activity, hyperphagia, abnormal lipid mobilization, abnormal fatty acid profile from the eye of the subject, ulcers and a glucosuria. One of skill in the art can note when the object of the method has been obtained by noting a reduction in glucose in the patient's blood or urine or an amelioration of symptoms such as normalization of blood pressure, disappearance of bulbous swellings around varicose veins, etc.

Any mode of administration can be used to deliver the extract. It can be added to a pharmaceutically acceptable carrier and systemically, orally, transdermally or topically administered to the subject. Therapeutic amounts can be empirically determined and will vary with the pathology being treated, the subject being treated and the toxicity of the form of the active fraction used in the therapeutic method. Active extract, fractions, compounds or compositions comprising one or more of the same in various forms can be delivered orally, intravenously, intraperitoneally, or transdermally. When delivered to an animal, the method is useful to further confirm efficacy of the extract, fraction, compound or composition comprising one or more of the same, for the disease sought to be treated. Appropriate animal models are known in the art. For the purpose of illustration only, an appropriate animal model is described in Experiment No. 1, infra. Using the animal model described in Experiment No. 1, Applicant noted that a single dosage corresponding to 70× the human daily dose was found to be non-toxic when applied per oral to 6 week-old outbred NMRI lean mice or 6 week to 11 week-old inbred C57BL/6J lean mice. The treatment regime consisted of applying a daily dose of a 7× human-daily-dose to the C57BL/KsBom-db (db/db) mice per oral for 6 weeks. During treatment, the test and control animals were maintained on the carbohydrate and fat-deficient Altromin C1009 diet. The extract lowered hyperphagia and facilitated weight loss in the treated Type II diabetes mouse model. Although the weight loss was not statistically significant, the treated animals had a significantly higher serum triglyceride content as compared to the control group showing that the treatment induced lipid mobilization from internal stores in the animals placed on severe calorie restriction. In addition, the fatty acid profile of the eye from the treated animals showed a significant reduction in total fatty acids and in all the major subclasses of lipids, a 33% reduction in estimated Stearoyl-CoA desaturase activity (P=0.039, compared with the untreated controls). Interestingly, the fatty acid mobilization that was observed at the end of the 6-week treatment was maintained after cessation of treatment for a further 5 weeks if the treated animals were maintained under calorie restriction. This coincided with an observed protection of the "brittle" pancreas in the db/db mice. In contrast treated mice that were later fed the richer standard Altromin 1314 diet post-treatment, lost these advantages.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents can be found below.

The extracts, fractions, compounds, compositions and pharmaceutical formulations of the present invention can be used in the manufacture of medicaments, food and health supplements, and for the treatment of humans and other animals by administration in accordance with conventional procedures, such as an active ingredient in pharmaceutical compositions.

It will be appreciated that appropriate dosages of the compounds and compositions of the invention may depend on the type and severity and stage of the disease and can vary from patient to patient. Determining the optimal dosage will generally involve the balancing of the level of therapeutic benefit against any risk or deleterious side effects of the treatments of the present invention. The extract, fraction, compound or composition comprising one or more of the same, compositions can be administered orally, intranasally, parenterally or by inhalation therapy, for example. It may be formulated into any suitable delivery means, examples of which include but are not limited to tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to active agent or extract of the present invention, the pharmaceutical compositions can also contain other pharmaceutically active compounds or a plurality of compounds of the invention.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Pharmaceutical compositions for topical administration according to the present invention may be formulated as an ointment, cream, suspension, lotion, powder, solution, paste, gel, spray, aerosol or oil. Alternatively, a formulation may comprise a patch or a dressing such as a bandage or adhesive plaster impregnated with active ingredients and optionally one or more excipients or diluents. Formulations suitable for topical administration in the mouth also include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for vaginal administration may be presented as pessaries, tampons, creams, gels, pastes, foams or spray formulations containing in addition to the active ingredient, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above recited, or an appropriate fraction thereof, of a drug ingredient.

It should be understood that in addition to the ingredients particularly mentioned above, the formulations of this invention may include other bio-active agents conventional in the art having regard to the type of formulation in question. For the purpose of illustration only, such additional bio-active agents include, but are not limited to sulphonylureas, e.g. chlorpropamide (the trade name: Meldijan, etc.), carbutamides (some 40 trade names), glybenchlamides (trade names: Euglukon, Glibenklamid Genericon, etc.) and biguanides which includes, e.g. phenyl-ethyl-biguanide (trade names: Phenformin, DB-Comb, etc.) as well as dimethyl-biguanides (trade names: Gluchopage, etc.). In yet a further embodiment, additional agents suitable of oral administration may be included in the compositions and formulations, e.g., sweeteners, thickeners and flavoring agents.

The extract, fraction, compound or composition comprising one or more of the same, may also be presented for use in the form of veterinary formulations, which may be prepared, for example, by methods that are conventional in the art.

This invention further provides a method for screening for a therapeutic agent for treating or ameliorating the symptoms associated with abnormal blood glucose, e.g., abnormally high levels of blood glucose such as that experienced by diabetic patients, by comparing the activity of a potential therapeutic against the therapeutic activity of the extract of this invention. In one aspect, the patient is suffering from diabetes Type II. The assay can also be used to screen new or alternative formulations or combinations of the extract with another active agent or therapeutic. The screen requires (a) the administration of the potential agent to a suitable animal model and (b) administering an effective amount of the extract, or a pharmaceutically acceptable composition containing the extract, to another suitable animal. The biomarkers of the therapeutic response of the animal(s) of step (a) to those of step (b) are compared. If any agent of step (a) provides a therapeutic response that is the same or similar extent as the model of step (b), it is a therapeutic agent for treating or ameliorating the symptoms associated with abnormal blood glucose in an animal. Suitable animal models include, but are not limited to the animal model described in Experiment No. 1, infra. or a human patient, e.g., a diabetic human patient.

Also provided is the use of the extract in the manufacture of a medicament for the treatment of diabetes.

A kit for treating or ameliorating the symptoms associated with abnormal blood glucose, e.g., abnormally high levels of blood glucose, also is provided by this invention. The kit includes a therapeutically effective amount of the extract and instructions for use. The kit is useful to treat disorders selected from the group consisting of Type II diabetes, abnormal steraroyl-CoA desaturase activity, hyperphagia, abnormal lipid mobilization, abnormal fatty acid profile from the eye of the subject, ulcers and glucosuria.

The following examples are intended to illustrate, but not limit the invention.

EXAMPLES

Experiment No. 1—A Novel Animal Model

Lipids constitute a major part of living cells where they provide the physical barrier that compartmentalizes cells and serve as a major storage form of energy in the liver and adipose tissue. Membrane lipids do not just form an inert framework for cells. Rather, fundamental roles are now recognized for membrane lipids and their bioactive derivatives in cell function, especially in the responses of the cell to external stimuli from hormones, neurotransmitters and growth factors. It is therefore not surprising that alterations in membrane lipid composition have been associated with specific disease conditions such as cystic fibrosis (Freedman et al. (2004) New Eng. J. Med. 350: 560-569), diabetes and obesity. Vessby B. (2000) Brit. J. Nutr. 83 Suppl.: S91-96.

However, there are conflicting reports in the literature as to the extent of the alterations and as to which tissue or organs best manifest the modifications. While increases in the saturated fatty acid (SFA) and the lower molecular weight polyunsaturated fatty acid (PUFA) contents have been associated with altered skeletal muscle insulin responsiveness in man, Clore et al. ((2000) Metabolism: Clinical and Experimental 49:2332-238) found an increase in the long chain PUFA (e.g. Arachidonic acid) and a lower linoleic acid content in serum of diabetics as compared to samples taken from healthy controls.

In order to establish the status of some of the parameters associated with lipid homeostasis in Type II diabetes model mice, the fatty acid (FA) content of tissues implicated in the pathophysiology of diabetes in mice was investigated. The tissue fatty acid composition of the genetically bred diabetic (db/db) and obese (ob/ob) mice with those from lean mice of the same age and fed on the same diet were studied. The tissues investigated for their FA profiles include adipose tissue, eye, liver, pancreas and skeletal muscle. The results show that while there was an accumulation of lipids in most of the different tissues from the obese mice, there was selectiveness in the deposition of lipids in the adipose tissue, eye and muscle of the diabetic mice, and suggested increase in stearoyl-CoA desaturase activity in the latter two tissues.

Experiment No. 1—Procedures

Animals

The study was performed under the guidelines approved by the Danish Animal Care and Use license. The experimental animals were male genetically bred C57BL/6Jbom-ob/ob (obese, n=4), C57BL/KsBom-db/db (diabetic, n=3) mice and the lean C57BL/6J inbred strain (n=4). The animals were purchased from Bomholtgaard Breeding and Research Centre Ltd., Ry, Denmark when they were 13 weeks old. The animals were kept in groups of 3-4 mice per cage, maintained on Altromin 1320 standard maintenance diet and housed in a room kept at 25° C. with a 12 h dark and 12 h light cycle.

Sample Collection

When the animals were 23 weeks old, they were fasted overnight. On the next day, the animals were weighed, ether anaesthetized and blood samples were collected by orbital puncture, before the animals were sacrificed. The blood samples were allowed to clot at room temperature (about an hour) and cleared serum samples were collected after high-speed centrifugation (3000 g) at 4° C. for 30 min. Serum insulin and glucagon contents were determined using Radio ImmunoAssay ("RIA") Kits, (Linco Research, Inc. Missouri, USA). Samples of the eye, liver (left anterior lobe), pancreas, skeletal leg muscle, and adipose tissue (around the testis) were taken from each of the animals and immediately frozen in liquid nitrogen and stored at −70° C.

FA Analysis

The total lipids in the tissues were extracted with chloroform/methanol, methylated and analysed by gas-liquid chromatography in a Hewlett Packard 5890 series II Chromatograph with flame-ionisation detection (Hewlett-Packard GmbH, Waldbronn, Germany), essentially as by described by Staarup and Hoy (2000) J. Nutr. 130:2802-2808. Briefly, the apparatus was fitted with a 60 m fused silica capillary column (SP-2380) and the injector and detector temperature were at 270° C. The carrier gas was helium. The initial oven temperature was 70° C. for 0.5 min and the temperature programming was as follows: 15° C. min$^{-1}$ to 160° C., 1.5° C. min$^{-1}$ to 200° C., maintained for 15 min, and 30° C. min$^{-1}$ to 225° C., which was kept for 5 min.

The amount of each type of fatty acid (% wt content of fatty acid multiplied by µg total fat per mg tissue) was quantified for the different tissues. The sum of the saturated fatty acids (SAT), monounsaturated fatty acid (MUFA) and PUFA were calculated for each sample and expressed as µg fatty acid mg$^{-1}$ tissue (or mg fatty acid mg$^{-1}$ tissue for adipose tissue). The activities of selected enzymes involved in fatty acid biosynthesis were estimated as the product to precursor ratios of the percentages of the individual fatty acids. The estimated fatty acid-related metabolic processes included the delta9 or Stearoyl-CoA desaturase activity estimated as the ratio of oleic acid [C18:1(n-9)] to stearic acid (C18:0) ratio, and delta6 desaturase that was calculated as the ratio of the sum of γ-linolenic acid (LNA, [C18:3(n-6)], dihomogamalinolenic acid (DGLA, [C20:3(n-6)] and Arachidonic acid (AA, [C20:4(n-6)]) to linoleic acid [C18:2(n-6)].

Statistics

The values are expressed as mean±standard errors. Statistical differences in the data were tested using ANOVA (non-paired t-tests) in Microsoft Excel. Values of p<0.05 were considered significant.

Results

Body Weights, Serum Insulin and Glucagon Levels

The body weights, serum insulin and glucagon levels from the mice are presented in Table 1. As expected, the ob/ob mice showed significant increases in body weight, when compared to the lean mice. There was no significant difference between the mean body weight of the diabetic mice and their lean counterparts. The ob/ob and db/db mice show the increased levels of insulin and glucagon and that are typical for the breeds (5); compare normal fasting ranges that are 0.5-2 ng/ml for insulin, and 50-150 pg/ml for glucagon, respectively.

TABLE 1

Body weight, serum insulin and glucagon of the mice (expressed ±SEM)

|  | Lean mice C57 BL/6J (n = 4) | Obese mice ob/ob (n = 4) | Diabetic mice db/db (n = 3) |
| --- | --- | --- | --- |
| Body weight (g) | 34.7 ± 0.5 | 65.2 ± 1.0 * | 34.9 ± 6.9 |
| Serum insulin (ng ml$^{-1}$) | 0.66 ± 0.30 | 130 ± 37 * | 7.4 ± 2.64 [a] |
| Serum glucagon (pg ml$^{-1}$) | 179 ± 15 | 233 ± 15 * | 439 ± 116 [a] |

* $P < 0.05$.
[a] The analysis was carried out on serum obtained from only 2 of the db/db mice.

Genetically Obese and Diabetic Mice Tissues Differ in how Monounsaturated Fatty Acids are Accumulated The relative amounts of the major classes of fatty acids for the adipose tissue, eye, skeletal muscle, pancreas, liver-triacylglyceride (liver-TAG fraction) and liver-phospholipid (liver-PL fraction) from the different mice are presented in FIGS. 1A, B, C, D, E and F, respectively. Generally, there was an increase in the total fatty acids and in particular SFA and MUFA in the tissues from the obese mice, as compared to that in both the lean and diabetic mice tissues. Thus, with the exception of the eye, significant increases in SFA and MUFA accumulation were observed in the obese mice tissues in comparison with values in the lean mice. Interestingly, the genetically diabetic mice only showed a significant increase in FA accumulation (especially MUFA) in adipose tissue, the skeletal muscle and in the eye, when compared to the FA content in the lean mice tissues (FIG. 1B).

Figure 2:
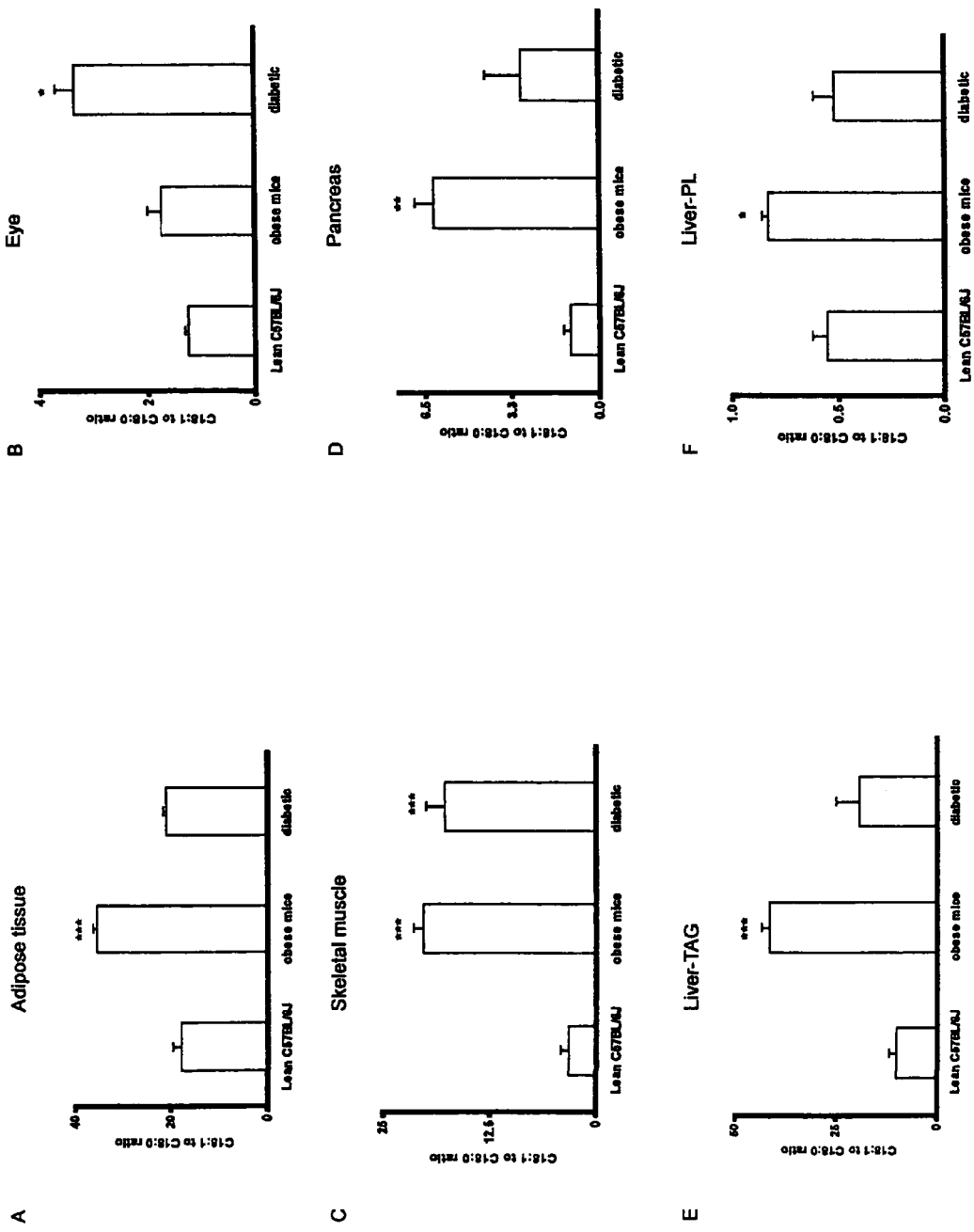
FIG. 2 compares estimated stearoyl-CoA desaturase activity (calculated as oleic acid to stearic acid ratios) in adipose tissue (A), eye (B), skeletal muscle (C), pancreas (D), liver-triglyceride (E) and liver-phopholipid fraction (F), respectively in lean, obese and diabetic mice. Data are expressed as mean±SEM values. Significant difference of data from obese and diabetic mice from that in the lean controls is expressed as *=$p<0.05$; =$p<0.01$; *=$p<0.001$.

Estimated Stearoyl CoA Desaturase Activity is Increased Differentially in ob/ob and db/db Mice Tissues In line with the above observations of MUFA accumulation, there was an increase in the calculated stearoyl CoA desaturase activity in most of the tissues from the obese mice (FIGS. 2A, B, C, D, E and F). For the diabetic mice, a significant increase in delta9 desaturation was only associated with the eye and skeletal muscle, which also had a marked accumulation of MUFAs (see above).

Figure 3:
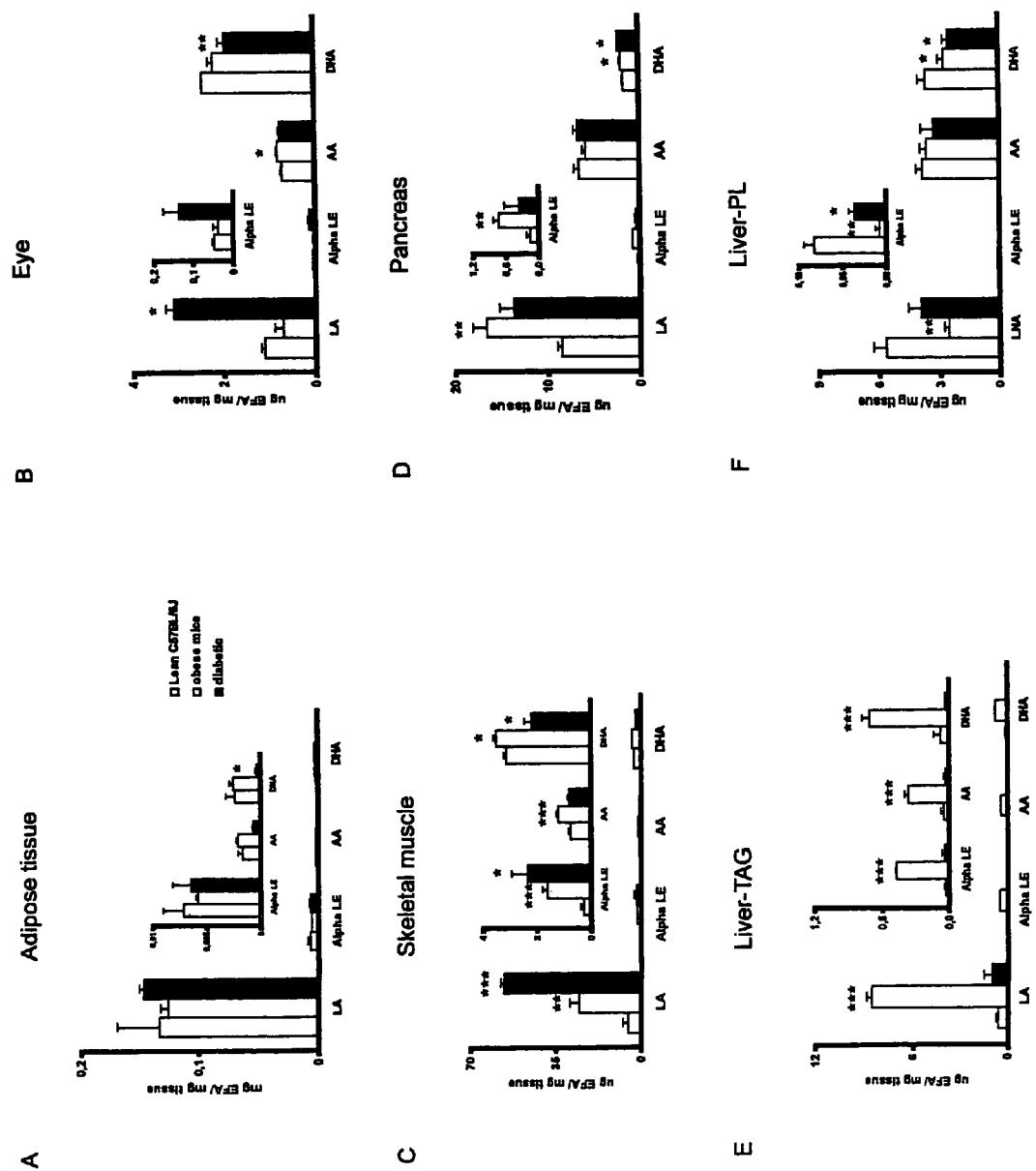
FIG. 3 compares the essential fatty acid contents (Linoleic acid, LA; Alpha-Linolenic acid, Alpha-LE; Arachidonic acid, AA; and docosahexanoic acid, DHA) in adipose tissue (A), eye (B), skeletal muscle (C), pancreas (D), liver-triglyceride fraction (E) and liver-phopholipid fraction (F), respectively from lean, obese and diabetic mice. Data are expressed as mean±SEM values. Significant difference of data from obese and diabetic mice from that in the lean controls is expressed as *=$p<0.05$; =$p<0.01$; *=$p<0.001$.

Genetically Obese and Diabetic Mice Differ in how and in what Type of Polyunsaturated Fatty Acids are Accumulated in Tissues The PUFA fraction was significantly increased in the pancreas, liver-TAG fraction and the skeletal muscle from the ob/ob mice when compared with the levels in the lean mice (see FIGS. 1 and 3). In the db/db mice, a significant PUFA increase was also evident in the skeletal muscle. While both the long and short chain forms of the PUFAs were accumulated in the obese mice tissues, the increase in the PUFA fraction in the diabetic mice muscle was mainly due to an accumulation of the short chain LA and alpha-linolenic acid (FIG. 3). Although the accumulation of the precursor n-6 LA did not coincide with a significant reduction in the longer chain n-6 product arachidonic acid (AA) in the db/db mice as compared with the lean mice, there was a significant reduction in the long chain n-3 DHA in the skeletal muscle and in other tissues from the db/db mice. The only exception here was the db/db pancreas that contained significantly higher amounts of DHA than was observed in the pancreas from the lean control animals (see FIG. 3).

Estimated Delta6 Desaturase Activity is Reduced in the Eye and Skeletal Muscle of the db/db Mice.

Figure 4:
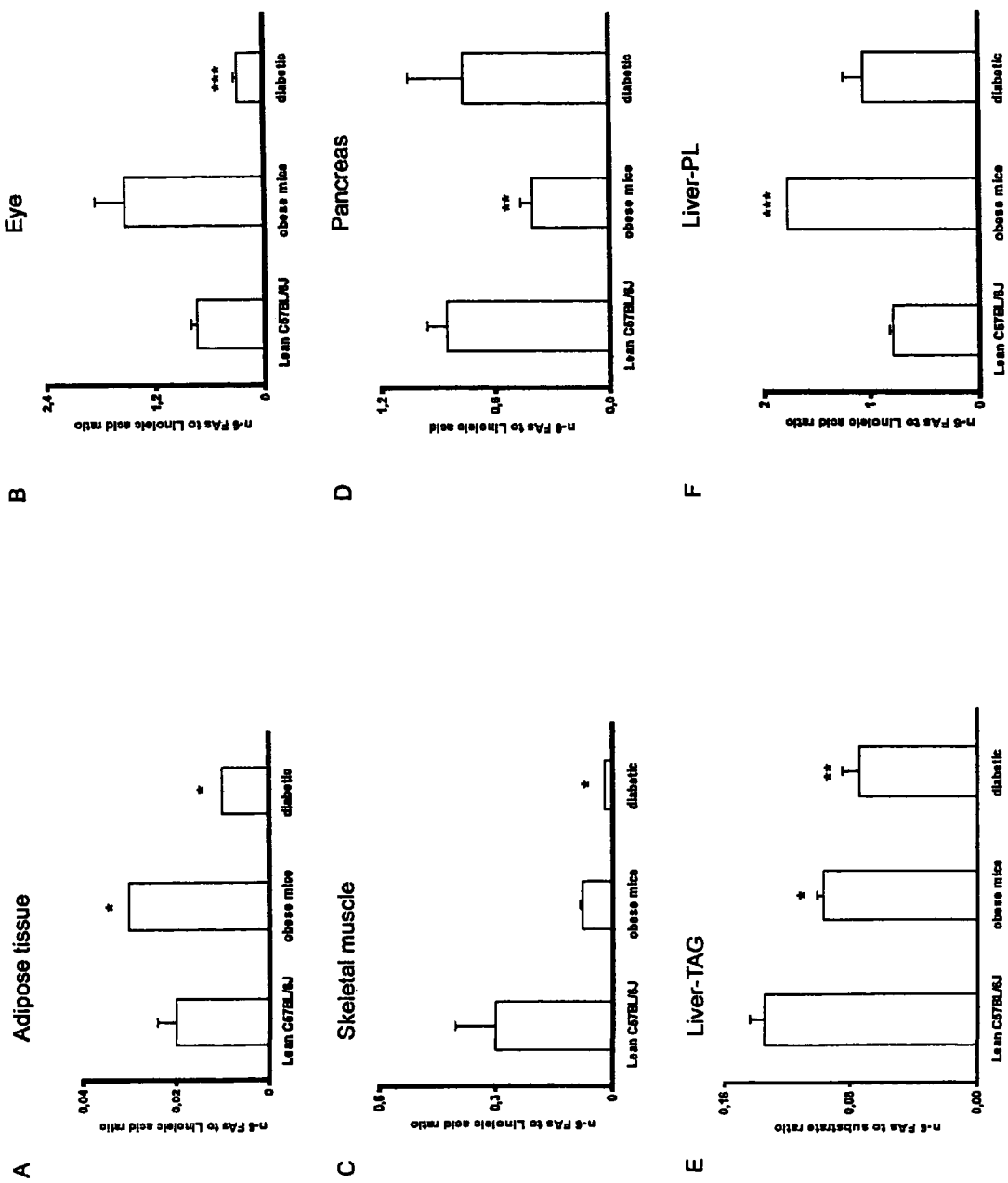
FIG. 4 compares estimated Δ6 desaturase activity (calculated as a ratio of the sum of α-linolenic acid, dihomogama-linolenic acid and arachidonic acid to linoleic acid content) in adipose tissue (A), eye (B), skeletal muscle (C), pancreas (D), liver-triglyceride fraction (E) and liver-phopholipid fraction (F), respectively in lean, obese and diabetic mice. Data are expressed as mean±SEM values. Significant difference of data from obese and diabetic mice from that in the lean controls is expressed as *=P<0.05; =P<0.01; *=P<0.001.
Figure 5:
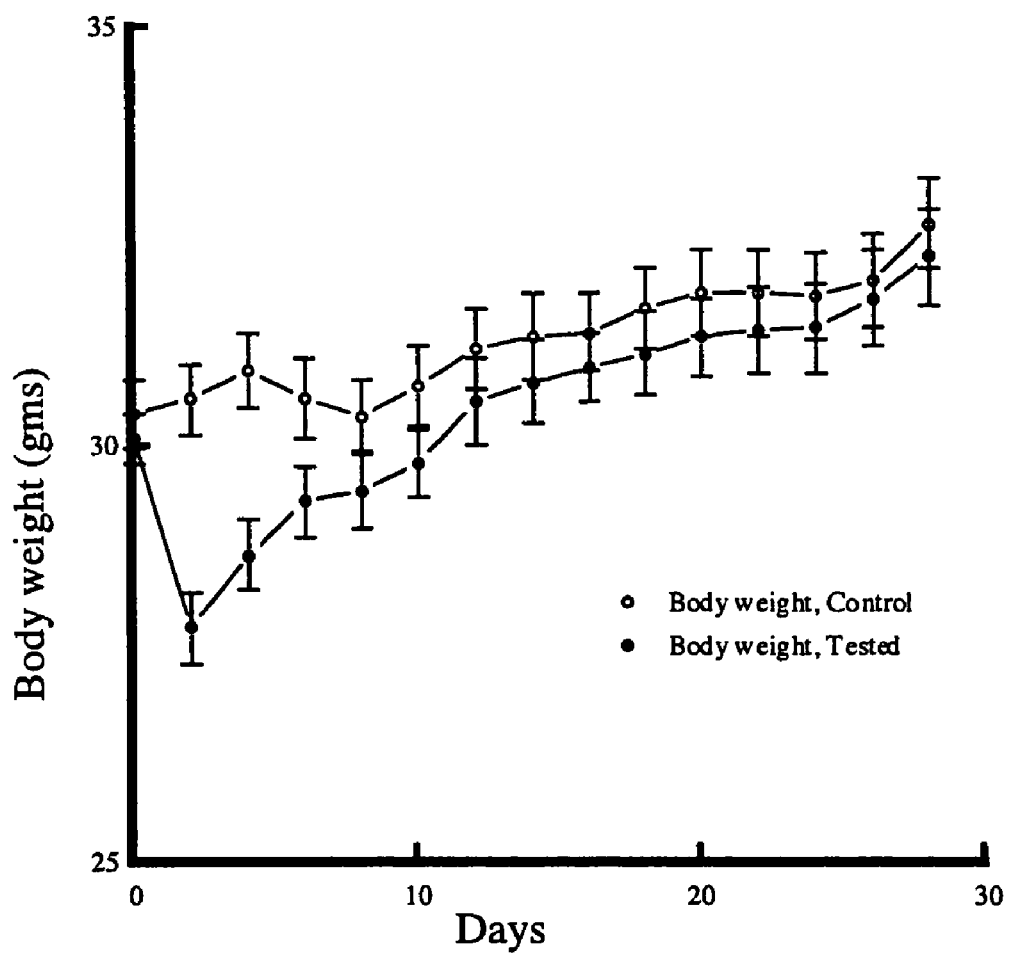
FIG. 5 shows the effect of the *Rauvolfia-Citrus* extract on body weight of 11 weeks old lean C57BL/6J mice, following a single administration of a 70× human-daily-dose.

With the exception of the pancreas and liver PL fraction, there was a reduction in the estimated delta6 desaturation activity in the tissues from the db/db mice (FIGS. 4A, B, C, D, E, and F). The reduction in delta6 desaturation could not be verified with an estimate of the delta4 desaturation (calculated as the ratio of DHA [C22:6(n-3)] to docosapentanoic acid DPA [C20:5(n-3)], as several of the tissues from the diabetic mice lacked detectible levels of DPA. However, the reduction in delta6 desaturation does coincide with significant reductions in DHA levels in the diabetic mice. In the obese mice, reductions in estimated delta6 activity were also calculated for the pancreas and liver-TAG fraction, while an increase was predicted for the adipose tissue and the liver-PL fraction (FIGS. 4D and E).

Discussion of Results

The liver and adipose tissue constitute the major tissues for storage, processing and distribution of caloric fuels in mammals. Under normal conditions, there is a dynamic interplay between these and other tissues in the body that is highly responsive to certain hormones and co-factors, and ensures that mammalian tissues maintain a constant flow of energy-rich fuels despite intermittent fasting periods. Type II diabetes or NIDDM results from a malfunction in the body's energy metabolism. The metabolic disturbances characteristic of NIDDM are increasingly being closely linked with alterations in lipid metabolism and obesity. Vessby (2000) New Eng. J. Med. 350:560-569; McGarry (1992) Science 258: 766-770. Obesity is characterised by an increased accumulation of tissue lipids.

This experiment shows that there is a clear distinction in tissue lipid distributions in the genetically diabetic db/db mice with a severe form of NIDDM and in the genetically obese ob/ob mice with the milder form of Type II diabetes, when compared to their lean counterparts. While the ob/ob mice accumulated SFA and MUFA in all the tissues examined with the exception of the eye, the accumulation of MUFA in the db/db mice was restricted to adipose tissue, the eye and skeletal muscle. Thus, the liver in severe mice diabetes appears to be spared against lipid accumulation. Instead, the excessively generated MUFA is deposited in other non-adipose tissue, such as the eye and muscle (see Table 2). Whereas diabetic retinopathy and its often associated lipid deposit on the retina have been reported (Curtis & Scholfield (2004) Diabetes-Metab. Res. 20:28-43), this distinction in eye tissue lipid accumulation between the ob/ob (representing mild NIDDM state) and db/db mice (representing severe NIDDM state) has not been documented in the literature.

Saturated fatty acids such as palmitic acid (C16:0) and stearic acid (C18:0) are synthesised in mammalian cells by the enzyme complex, FA synthetase (FAS) which uses the building blocks generated by the rate limiting enzyme, acetyl CoA carboxylase. As stearic acid and to a lesser extent palmitic acid, are water insoluble (Kim & Ntambi (1999) Biochem. Biophys. Res. Comm. 266:1-4), the end products of de novo FA biosynthesis in mammals are often converted to their MUFA forms, oleic acid (C18:1) and palmitoleic acid (C16:1), respectively by stearoyl-CoA desaturase. Enoch et al. (1976) J. Biol. Chem. 251:5059-5103. However, in the high fat-diet that is common in most developed nations, some of the excess fat that is consumed is not catabolized, but simply stored in tissues. Indeed, de novo FA synthesis and remodelling by deacylation/reacylation of existing lipids occur at similar rates in rat hepatocytes. Schmid et al. (1995) Arch. Biochem. Biophys. 319:168-176. In this study, the estimated stearoyl-CoA desaturase activity was enhanced in the tissues (with the exception of the eye) from the obese mice. In the diabetic mice, the increase in stearoyl-CoA desaturase activity was only associated with the eye and muscle (namely in two of the tissues with increased MUFA accumulation). A central role for the enzyme in FA accumulation in obesity and in the development of Type II diabetes has been confirmed by the finding that the loss of one of the two mice SCD genes led to a reduction in body adiposity and resistance to diet-induced weight gain. Ntambi et al. (2002) Proc. Natl. Acad. Sci. USA 99:11482-11486. In addition, the SCD1 −/− animals had increased insulin sensitivity resulting from an elevation in cellular factors involved in insulin signaling. Rahman et al. (2003) Proc. Natl. Acad. Sci. USA 100:11110-11115. Indeed the anti-Type II diabetes drugs, thiazolidinediones have been shown to exert part of their anti-diabetic effects via the PPARγ receptor by repressing SCD1 gene expression. Kurebayashi et al. (1997) Diabetes 46:2115-2118.

One of the long-term complications associated with NIDDM is poor wound healing. Colville-Nash & Willoughby (1997) Mol. Med. Today 3:14-23. Essential fatty acids (EFAs) are important precursors for several eicosanoids and docosanoids that have pro-inflammatory and anti-inflammatory effects, respectively. Hence, the alterations in the EFAs in the two NIDDM model mice were examined. The PUFA fraction is increased in the pancreas, liver-TAG and skeletal muscle, but reduced in the liver-PL fraction of the ob/ob mice, as compared to the lean mice. An increase in the PUFA fraction was also observed for the skeletal muscle from the db/db mice. In contrast to the pattern of PUFA increases in the ob/ob mice, the shorter chain PUFAs—LA and alpha-linolenic acid—are solely responsible for the PUFA increase in the muscle of the db/db mice. In adult humans, insulin resistance in obesity and diabetes has been associated with relatively low proportions of the long chain PUFAs in skeletal tissue (Borkman et al. (1993) New Engl. J. Med. 328:238-244; Storlien et al. (1996) Lipids 31: S261-S265), and in red blood cells (Min et al. (2004) Diabetologia 47:75-81) as compared to the amounts found in lean controls.

The biosynthesis of the long chain essential PUFAs from LA and alpha-linolenic acid in mammalian cells is driven by the delta6 and delta5 desaturases in a series of enlongation and desaturation steps. In the absence of insulin (as is the case in untreated type I diabetes), both enzyme activities are down regulated. Brenner (2003) Prostaglandins Leukot. Essent. Fatty Acids 68:151-162. The condition is corrected on administration of insulin. Mercuri et al. (1967) Lipids 2: 284-285; Suresh & Das (2003) Nutrition 19:213-228. Although the activity of the enzymes have been well studied in type I diabetes, there is a paucity of data concerning their levels and activities in Type II diabetes. In this study, an enzyme activity estimation based on the n-6 PUFA product to substrate ratios suggested that while the delta6 desaturase activity may be increased in some of the obese mice tissues, the enzyme activity might be reduced in most of the tissues from the db/db mice (see FIG. 3). The only exception to the db/db trend was the pancreas where the estimated delta6 activity was increased in comparison with the lean controls, and neither the estimated delta6 desaturase activity (FIG. 3D) nor delta4 desaturation calculated as DHA to DPA ratio, differed significantly from the levels observed in the lean mice. Although the significant decrease in estimated delta6 desaturase activity in the other tissues of the db/db mice coincides with a significant reduction in DHA levels (FIG. 4), AA contents were not reduced when compared to the levels in the lean mice. Furthermore, the lack of distinction between triacylglycerol and phopholipid fractions in most of the tissues analysed here makes it difficult to ascertain whether the increases in LA or alpha-linolenic are simply due to increases in triacylglycerol that favours accumulation of the short chain PUFAs. In the ob/ob liver, the accumulated lipid appears solely in the triacylglycerol fraction.

Nevertheless, the alterations in the tissue content of EFAs in Type II diabetes can have some far reaching effects for the prognosis of Type II diabetes. On the one hand, the long chain PUFA DHA that is scarce in severe NIDDM, is one of the main precursors for docosatrienes and resolvins that are beneficial for the resolution of both acute and chronic inflammation (Hong et al. (2003) J. Biol. Chem. 278: 14677-14687), as well as for disorders involving an inappropriately activated auto-immune response. Calder (1997) Ann. Nutr. Metab. 41:203-204. On the other hand, a lipid based-molecule derived from LA by the action of 15-lipoxygenase-1,13-S-hydrocyoctadecadienoic acid has been shown to be an apoptotic agent. Shureiqi et al. (2003) Proc. Natl. Acad. Sci. USA 100:9968-9973; Nixon et al. (2004) Prostaglandins Leukot. Essent. Fatty Acids 70: 7-15. Taken together, the reduction in DHA combined with the increase in LA might contribute to enhancing some of the long-term complications of diabetes associated with the eye and in poor wound healing in skeletal muscle. Recently, Brenner and associates (Brenner et al. (2003) Lipids 38:733-742; Montanaro et al (2003) Lipids 38:827-832) published work showing that delta6 and delta5 desaturase activities are increased in hepatic microsomes of two other Type II diabetes model animals.

Only the estimates for delta6 desaturase activity in liver-PL fractions of the genetic diabetic ob/ob micee studied here agree with the actual enzyme activity measurements in the rat Type II diabetes model animals.

FA metabolism is cell-specific and the both the stearoyl CoA desaturase and delta6 desaturase activities considered in this study are estimates. It is therefore interesting to determine and compare the actual levels of expression and activities of the enzymes involved in the lipid homeostasis in tissues taken from the 3 groups of C57BL mice. There were clear differences in lipid contents and composition in the tissues from the lean, obese and diabetic mice based on the same C57BL-genotype and fed the same diet. Thus, with the exception of the eye, there was an accumulation of SFA and MUFA in all tissues from the genetically obese mice. In the db/db mice with the more severe form of NIDDM that is associated with several long-term complications of Type II diabetes. the liver was spared the lipid accumulation and fatty acids-build up of the MUFA subclass was restricted to the eye, adipose tissue and skeletal muscle. Both the mild and severe forms of NIDDM were associated with PUFA accumulation in the skeletal muscle, although the short chain PUFAs were predominantly responsible for the increases in severe NIDDM. These distortions in the tissue lipids in Type II diabetes may define the pathophysiology of the disease.

Experiment No. 2—Preparation and Administration of Extract An Animal Study

Materials and Methods

Plant Material and Preparation of the *Rauvolfia-Citrus* Infusion.

The leaves attached to young stems of *Rauvolfia vomitoria* and fresh fruits of *Citrus aurantium* were collected in Auchi and Ihievbe in northern Edo state of Nigeria (situated between latitude 70 north of the equator and longitude 60 20' east). A combination of washed dried foliage (total weight, 400 g) was arranged in alternate layers with quartered whole citrus fruits (total wet weight 2 kg), in a large aluminium pot. The plant material was then covered with 8 liters of tap water, brought to the boil, and allowed to simmer covered, at low heat for 1 h. The resulting golden coloured fluid was cooled to room temperature and filtered through coarse filters. The spent plant material was rinsed with 3 liters of water, boiled as before and the resulting tea was also filtered and pooled with the first lot collected earlier and frozen at −20° C. The total yield was typically 7.5 liters. The pooled plant extract was freeze-dried and the yield was typically 12 g dried extract from 1 liter.

Animal Models and Housing Conditions.

The experimental animals used in the treatment experiments were male inbred diabetic C57BL/KsBom-db mice. The mice are characterised by obesity, hyperphagia, temporal hyperinsulinaemia, degeneration of the pancreatic β-cells with age and hyperglycemia. Due to the insulin resistance observed in these mice, they are considered models of Type II non-insulin dependent diabetes. The db gene has been identified as coding for one of the different mice forms of leptin receptors expressed in the hypothalamus. Lee et al. (1996) Nature 379:632-635. Leptin is a hormone secreted by adipocytes that has pleiotypic effects on a number of body systems including reproduction and metabolism. Chehab et al. (1996) Nature Genetics 12:318-320. A total deficiency in leptin or resistance of the body to the effects of the protein can lead to the development of severe obesity. Ahima et al. (1996) Nature 382:250-252. The test animals were purchased when they were 5 weeks old, fed on standard Altromin mice/rat diet until they were 11 weeks old when the treatment was started. During treatment, both test and control animals were placed on calorie restriction by being fed with the carbohydrate and fat deficient Altromin C1009 diet.

For the toxicity tests, the *Rauvolfia-Citrus* infusion was tested on lean 6 weeks and 11 weeks old C57BL/6J inbred mice, as well as on lean 6 weeks old out-bred NMRI mice. The animals were fed on Altromin 1320 standard mice/rat maintenance diet for the duration of the toxicity experiment.

All the animals were purchased from Bomholtgaard Breeding and Research Centre Ltd., Ry, Denmark; housed in groups of 4 per cage, under controlled environmental conditions (temperature 25±1° C., relative humidity 55±5%, with a 12 h dark and 12 h light cycle and air changed 10 times/h). The animals were allowed free access to water and the feed stipulated above. Housing and caring followed national guidelines, and the Danish National Animal Ethics Committee approved the study. The study and all procedures were performed under the guidelines approved by the Danish Animal Experimental Inspectorate.

Toxicity Tests

The recommended maximum human dose is 3 average drinking-glassfuls per day. On the basis of an average volume of 750 ml per 70 kg body weight, dried extract derived from 770 ml and corresponding to 70 times the human daily dose was administered per kg mice. The 70 times measure allows for the factor 10 by which the metabolic rate in mice is faster than that in man, and an extra factor of 7 to create an overdose. The concentrated extract was administered in one dosage per oral using a mouse gavage. The animals were observed continuously for 2 hours following administration, allowed access to water and food ad libitum, and monitored every 2 days for body weight gain or loss, as well as for food and water intake per cage. The controls and the test groups were also monitored weekly for unfasted blood glucose contents, using the Boerhinger Mannheim (Reflolux S) sticks.

Treatment Regimen

Plant extract corresponding to 10 times the maximum human-daily-dosage was applied daily per oral to the diabetic mice, in a total volume of 0.5 ml using a mouse gavage for a period of 6 weeks. Control mice received the same volume of water. All the animals were observed daily for 1 hour after drug or water administration for gross behavioural changes, allowed free access to water and food, monitored every 2 days for body weight, food and water intake. Unfasted blood glucose content was also measured weekly.

Assessing 'Curing Effect' of the Treatment and Effect of Post-treatment Diet

In the traditional application of the *Rauvolfia-Citrus* treatment, the patients are advised to adhere to a healthy diet (low in sugars and fats) and to keep alcohol consumption to a minimum. The 'curing effect' of the treatment was accessed in 2 groups of db/db mice treated exactly as described in the treatment regime above. Each of the 2 groups also consisted of 10 test and 10 control mice. After the 6-week treatment period, one group was maintained on the poorer Altromin C1009 diet, while the second group was fed the richer standard Altromin 1314 diet for a 5-week period without further treatment.

Sample Collection and Analyses

At the end of the specified duration of the experiments, the mice were ether anaesthetized, and blood samples were collected by orbital puncture. The animals were then sacrificed and the organs were dissected out. The blood samples were allowed to clot at room temperature (about an hour) and cleared serum samples were collected after high-speed centrifugation at 4° C. for 30 min. Serum glucose, triglyceride and cholesterol contents were determined for the blood serum samples on the Boehringer Mannheim/Hitachi analytical system. Serum insulin and glucagon content were also determined using the Rat Insulin and Glucagon RIA Kits (Linco Research, Inc.).

The weights of the kidney, liver, pancreas and spleen were determined for the animals and specimens of these tissues, as well as the eyes were frozen in liquid nitrogen and stored at −70° C.

The fatty acid profiles of the eyes from treated and control animals were later determined as earlier described in Experiment No. 1.

Statistical Analysis

Values are expressed as mean±SD (and sometimes as standard errors). Statistical differences in data from the test and control groups were tested using ANOVA (non-paired t-tests) in Microsoft Excel. Values of $P<0.05$ were considered significant.

Experiment No. 2—Results

Toxicity Tests

Upon administration of the single 70× human dose/g mouse weight, the animals were observed to be very still for the first hour. By the second hour following the drug intake, all the tested animals were observed to become more awake.

By the following day, all the test mice were as active as those in the control groups. However, there were no significant differences in final body or organ weights, serum triglyceride and cholesterol contents in control compared to the toxicity tested 6 weeks old C57BL/6J and NMRI mice, 4 weeks after administration of the plant extract. Although the treated C57BL/6J mice had significantly higher serum glucose content at the end of the 4 weeks observation period, the serum glucose values of both test and control strains was in the normal range (Table 2). This result confirmed that the Rauvolfia-Citrus extract is not toxic to young mice of at least 2 breeds.

TABLE 2

Toxicity tests Results: Body weight, serum triglyceride, cholesterol, and glucose content in 6-week old C57 6J and NMRI mice given a single administration of a 70× human-daily-dose. The parameters that showed significant differences between the control and tested mice are highlighted.

| Mice group | Body weight | Triglyceride | Cholesterol | Glucose |
|---|---|---|---|---|
| C57 6J (control) | 29.5 ± 1.6 | 1.36 ± 0.29 | 2.43 ± 0.26 | 5.56 ± 1.37 |
| C57 6J (70× human-dose) | 28.6 ± 2.0 | 1.25 ± 0.34 | 2.56 ± 0.29 | 6.83 ± 0.88* |
| NMRI (control) | 38.1 ± 2.8 | 1.80 ± 0.37 | 3.67 ± 0.41 | 8.71 ± 1.13 |
| NMRI (70× human-dose) | 38.0 ± 3.8 | 1.74 ± 0.39 | 3.77 ± 0.58 | 9.37 ± 1.45 |

*$P < 0.5$.

Figure 6:
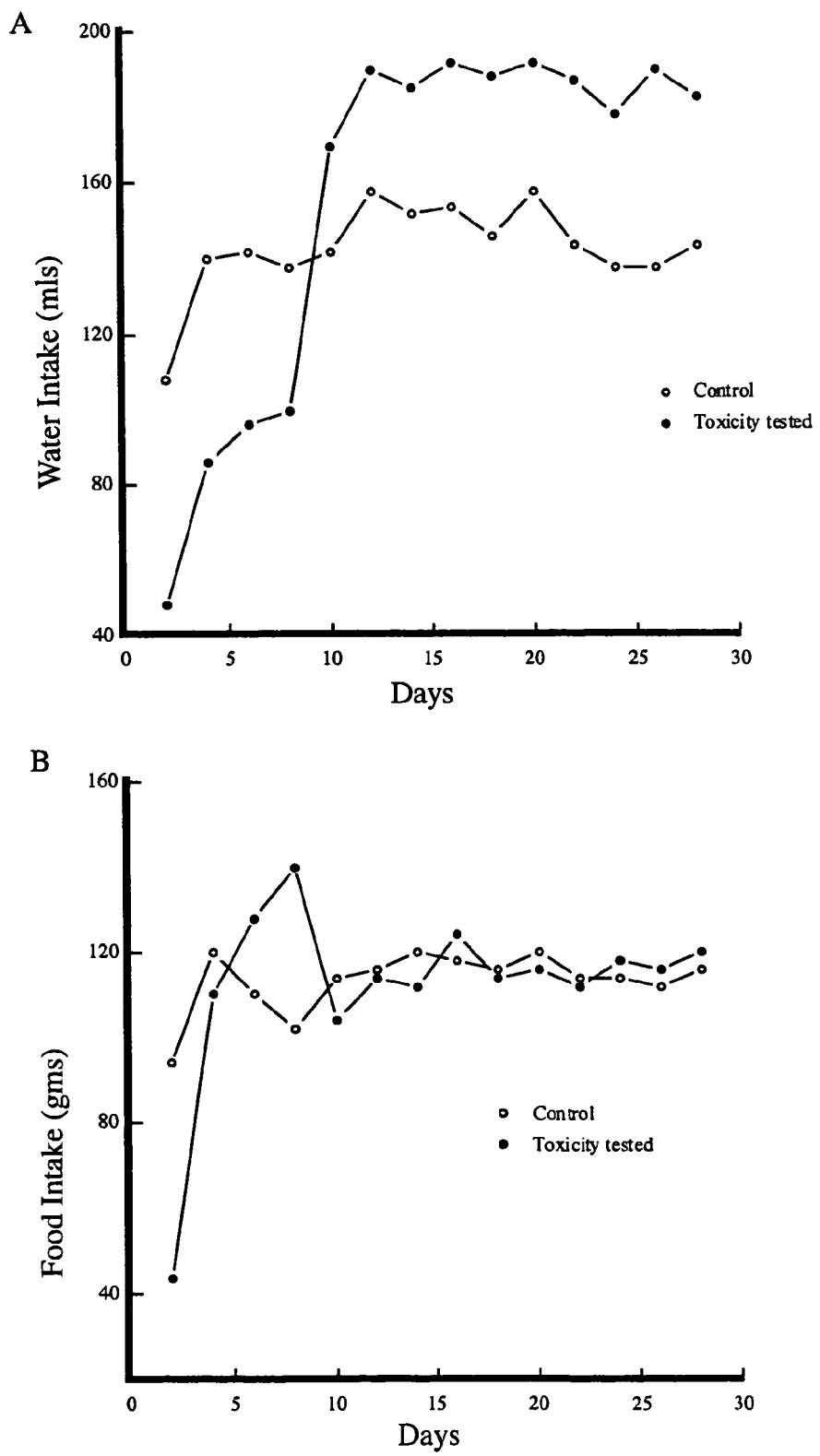
FIG. 6 shows the effect of the *Rauvolfia-Citrus* extract on water (A) and food (B) intake in 11 weeks old lean C57BL/6J mice, following a single administration of a 70× human-daily-dose.
Figure 7:
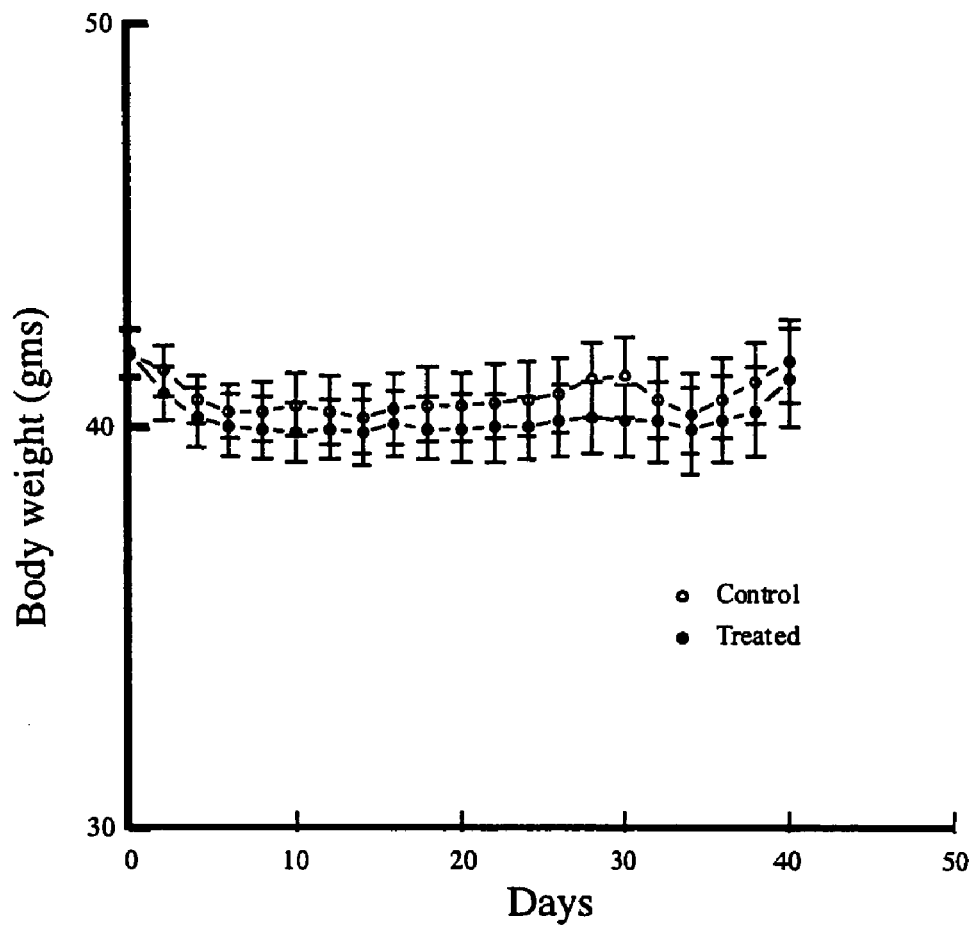
FIG. 7 shows the effect of the *Rauvolfia-Citrus* extract on body weight of 11 weeks old diabetic obese C57BL/KsBom-db/db mice, following treatment with a daily application of 7× human-daily-dose for 6 weeks.

In the toxicity tested 11 weeks old C57BL/6J mice, there was a significant difference in the weight gain in the treated group as compared to the control animals (FIG. 6). The difference was more noticeable just after application of the extract. This is reflected in the fact that the treated group ate less and drank less than those in control group in the observation period (FIGS. 7A and 7B). As the toxicity tested older C57BL/6J mice showed statistically significant smaller mean liver weight and a higher (albeit normal levels) serum glucose content, as compared to their control littermates at the end of the 4-week observation period (see Table 4), it was concluded that although the plant extract is not toxic to the older mice, it probably affects some metabolic processes in the liver of older mice.

TABLE 3

Toxicity tests results: Body and organ weights, serum triglyceride, cholesterol and glucose contents in 11 weeks old C57 6J mice given a single administration of a 70× human-daily-dose. The parameters that showed significant differences between the control and tested mice are highlighted.

| Parameter | 11-week old C57BL/6J mice (control) | 11-week old C57BL/6J mice (test) |
|---|---|---|
| Body weight | 32.7 ± 2.0 | 32.3 ± 2.0 |
| Liver weight | 1.59 ± 0.13 | 1.43 ± 0.22* |
| Kidney weight | 0.18 ± 0.02 | 0.18 ± 0.02 |
| Spleen weight | 0.10 ± 0.02 | 0.10 ± 0.05 |
| Pancreas weight | 0.43 ± 0.06 | 0.42 ± 0.03 |
| Serum Triglyceride | 1.343 ± 0.154 | 1.346 ± 0.306 |
| Serum Cholesterol | 2.6 ± 0.2 | 2.6 ± 0.2 |
| Serum glucose | 6.89 ± 0.96 | 7.64 ± 0.95* |

*$P < 0.5$.

Treated Diabetic Mice Lost Weight

Figure 8:
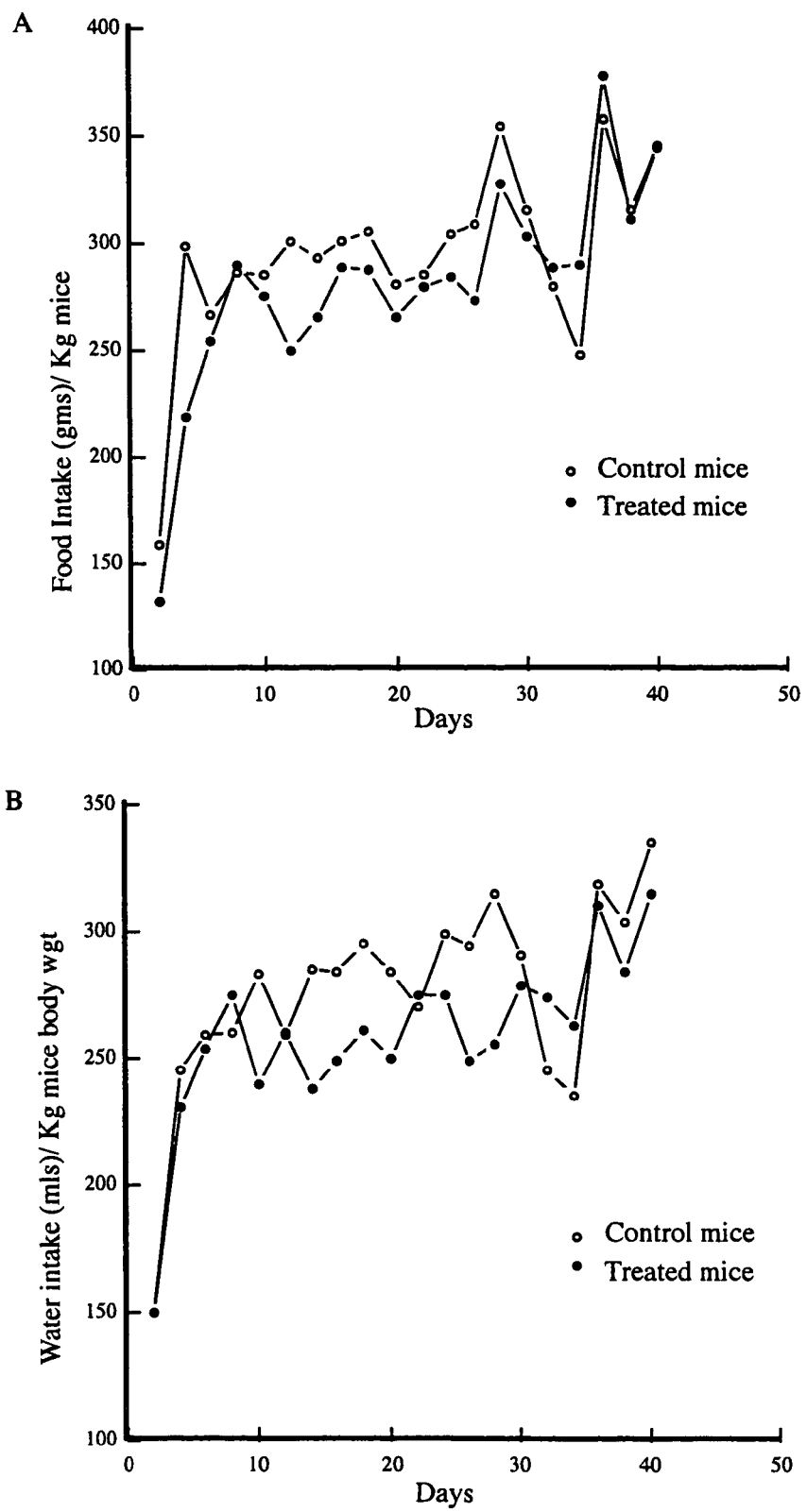
FIG. 8 shows the effect of the *Rauvolfia-Citrus* extract on food (A) and water (B) intake in 11 weeks old diabetic C57BL/KsBom-d/db mice, following treatment with a daily application of 7× maximum human-daily dose for 6 weeks.

In the treatment experiment, both the treated and control db/db mice lost some body weight following the shift to the poorer diet. However, the weight loss in the treated group was significantly higher than that observed in the control group (see FIG. 8). This may have arisen because the treated mice drank less and ate less as compared to their control littermates (see FIGS. 9A and 9B).

Treated Mice Showed Normoglycaemia and Signs of Fat Mobilization

At the end of the 6-week treatment period, the treated group showed a serum glucose level that was closer to the normal range as compared to the values for the control mice. Interestingly, the treated group also showed significantly higher serum triglyceride values although both groups still had very high serum insulin and glucagon levels (see Table 3). The increase in serum triglyceride coincided with a 36% reduction in the total fatty acid content in the eyes of the treated mice (see FIG. 10A), as compared to the untreated controls. In particular, the reduction in total fatty acid content was reflected in a 25%, 45% and 31% reduction in total saturated fatty acids, MUFAs and PUFAs, respectively. The reduction in the PUFA content of the treated mice eyes seemed to be mainly due to a 62% reduction in the linoleic acid content.

Accompanying these significant reductions in fatty acid contents were a 33% reduction in the estimated Stearoyl CoA desaturase activity and a 72% increase in the estimated delta6 desaturase activity in the treated mice as compared to their untreated control littermates. The amounts of each fatty acid (expressed as % of total fatty acids per mg tissue) in the eye samples from the treated and untreated control mice are presented in the Microsoft Excel chart attached as Appendix I.

Effect of Diet on the 'Cure' Post-treatment

At the end of a 5-week post-treatment observation period, the control mice that were maintained on the poor Altromin C1009 diet had lowered mean body weight, serum glucose, triglyceride and insulin values when compared to the values in the treated mice fed the same diet. Interestingly, the mean pancreas weight was significantly higher in the treated mice (see Table 4), suggesting that the treatment combined with a low calorie-diet may have slowed down the degeneration of pancreatic β-cells that is characteristic of the C57BL/Ks-Bom-db mice. In contrast, the mice that were fed on the richer standard Altromin 1314 diet post-treatment promptly put on weight such that at the end of the 5 week observation period, there were no differences in the serum glucose and triglyceride values between this group of treated and control mice.

Experiment No. 2—Discussion

The potential for toxic effect of the Rauvolfia-Citrus herbal remedy was studied on in bred and out bred lean mice. Apart from a slowing down of activity within the first day of the application of the drug, there were no significant differences in gross reactions and in the monitored parameters in 6 weeks old lean outbred NMRI mice or in the inbred C57BL/6J mice given a single administration of a 70× human-daily-dose. R.

*vomitoria* has a strong sedative effect that is used traditionally to calm psychiatric patients (Sofowora (1982) Medicinal Plants and Traditional Medicine in Africa, Wiley & Sons, Winchester, pp 75-76). The drowsiness induced with the high single dose may therefore be due to these sedative compounds contributed by the *R. vomitoria* fraction. However, the application of the same dosage to 11 weeks old C57BL/6J mice gave rise to higher serum glucose and smaller liver weights. The serum glucose is still in the normal range and the smaller liver weights observed in the tested group suggests that although the high dose of the extract is not toxic for older mice, it may be affecting some metabolic processes that are perhaps not present or important in younger mice.

At the end of a 6-week treatment period, the treated db/db mice showed a modest body weight loss and a normalization of their blood glucose. Both control and test mice showed improvements in the weekly glucose tolerance tests, as compared to the pre-treatment status. This suggests that the improvement in glucose clearance may be as a result of the calorie restriction imposed by the Altromin C1009 diet Caloric and nutritional information for this diet is available at the web site having the address altromin.de/cgi-bin/diets2.cgi?ansichtsid=C10009&ansicht=normal&diaetart=diaetart=sonder. Compare the standard Altromin 1320 diet available at the web address altromin.de/cgi-bin/diets2.cgi?ansichtsid=1320&ansicht=normal&diaetart=standard. Nevertheless, the final serum non-fast glucose was significantly lower with the treated mice. Thus, the treatment must have improved the insulin sensitivity of the treated mice beyond that which would be achieved by calorie restrictions alone.

As the mice were not being fed a lipid supplement, the significant increase in serum triacylglyceride in the treated db/db mice was interpreted to be due to an increase in fatty acid mobilization from internal stores. This postulate is supported by the significant reduction in fatty acid deposits in the treated mice eye (See FIG. 10A). *Citrus aurantium* has been reported as containing beta agonists that aid weight loss and enhance thermogenesis. Preuss et al. (2002) J. Med. 33:247-264. Beta agonists act on peroxisome proliferator-activated receptors (PPARs) decreasing plasma lipids and insulinaemia in obese animals. Grimaldi (2003) Biochem. Soc. Trans. 31:1130-1132. PPARs are molecular censors of dietary fatty and serum lipoproteins and are central to controlling many cellular and metabolic processes including development, proliferation, differentiation and lipid homeostasis. This data combined with the data generated and reported in Experiment No. 1, supra, certainly support the hypothesis that the *Rauvolfia-Citrus* treatment reverses this trend in the diabetic lipid homeostasis. The release of fatty acids from internal deposits is mediated by triacylglycerol lipase. Triacylglycerol lipase is in turn activated via cAMP-stimulated phosphorylation carried out by protien kinase. The released fatty acids are then transported via the blood stream to tissues for disposal by beta-oxidation in mitochondria with the help of carnitine. Although it is yet to be determined what the structure(s) of the active compound(s) in the plant extract are, the dependence of successful treatment on a calorie restriction would suggest that this cAMP-enhancing condition could be a likely scenario for the anti-diabetic effect of the *Rauvolfia-Citrus*-based herbal remedy. The proposed scenario also fits with that proposed for beta agonists in effecting weight loss and thermogenesis. Preuss et al. (2002) J. Med. 33:247-264, and this data that suggest significant decreases in Stearoyl-CoA desaturase activity upon treatment.

The results from Experiment No. 1 show that several tissues in Type II diabetes show an insufficiency in the long chain polyunsaturated fatty acids, docosahexanoic acid. The estimated increases in delta6 desaturase activity reported in this study following treatment of the genetically diabetic mice with the plant extract, could lead to the generation of the long chain polyunsaturated fatty acids that are essential for proper response to and resolution of tissue inflammation. If the same process occurs in humans, it could explain the association of the treatment with healing as reported in the Nigerian diabetic patients who had used the medication. However, the reduction in eye fatty acid content was significant for all classes of fatty acids. This means that in spite of a reduction in linoleic acid content, combined with an estimated enhancement in delta6 desaturase activity, there was no accumulation of the long chain PUFAs. Indeed, there was a significant albeit small reduction in arachidonic acid in the treated animals. As the eye lipids were not separated into triacylglycerol and phospholipid fractions, it is difficult to ascertain if the reduction in linoleic acid was mainly from a triacylglyceric acid pool. Indeed, the lack of increases in the arachidonic acid fraction would support the hypothesis that the linoleic acid pool is being mobilized along with the accumulated MUFAs. Thus, taking into consideration that the test animals were being fed a very poor diet, the results may look different if the treatment is combined with a PUFA diet supplement.

When the animals were kept under further calorie restrictions for a 5 week period post-treatment, there was still evidence of lipid mobilization as judged by increased serum triglyceride content. Interestingly, this coincided with a protection of the 'brittle' db/db pancreas typical of this breed of mice.

TABLE 4

Effect of *Rauvolfia-Citrus* extract on body and organ weights, serum triglyceride cholesterol, glucose, insulin and glucagon in bred diabetic C57BL/Ks-db mice after 6 weeks of treatment and the C1009 Altromin diet. Insulin and glucagon values are expressed as ng ml$^{-1}$ insulin ± SEM and pg ml$^{-1}$ glucagon ± SEM, respectively. The parameters that showed significant differences between the control and tested mice are highlighted.

| Parameter | C57BL/KsBom-db mice (control) | C57BL/KsBom-db mice (treated) |
|---|---|---|
| Body weight | 39.4 ± 3.1 | 38.72 ± 3.7 |
| Liver weight | 1.08 ± 0.14 | 1.04 ± 0.12 |
| Kidney weight | 0.172 ± 0.01 | 0.167 ± 0.029 |
| Spleen weight | 0.072 ± 0.031 | 0.063 ± 0.018 |
| Pancreas weight | 0.309 ± 0.07 | 0.30 ± 0.07 |
| Serum Triglyceride | 1.93 ± 0.56 | 3.64 ± 2.06* |
| Serum Cholesterol | 2.97 ± 0.21 | 3.02 ± 0.23 |
| Serum glucose | 10.77 ± 2.25 | 8.4 ± 1.49* |
| Serum Insulin | 11.55 ± 1.89 | 15.3 ± 1.07 |
| Serum glucagon | 258 ± 39.1 | 340 ± 36 |

*P < 0.5.

TABLE 5

Effect of diet on the 'curing effect' of the treatment in C57BL/Ks-db mice maintained for 5 weeks post-treatment on the poor C1009 and richer standard 1314 diet without further drug administration. Insulin and glucagon values are expressed as ng ml$^{-1}$ insulin ± SEM and pg ml$^{-1}$ glucagon ± SEM, respectively. The parameters that showed significant differences between the control and tested mice are highlighted.

| Parameter | db/db mice (control) fed Altromin C1009 | db/db mice (treated) fed Altromin C1009 | db/db mice (control) fed Standard Altromin 1314 | db/db mice (treated) fed Standard Altromin 1314 |
|---|---|---|---|---|
| Body weight | 34.9 ± 6.2 | 37.7 ± 3.2 | 51.8 ± 2.3 | 48.3 ± 3.4 |
| Liver weight | 1.07 ± 0.09 | 1.05 ± 0.4 | 1.72 ± 0.23 | 1.62 ± 0.2 |
| Kidney weight | 0.17 ± 0.03 | 0.17 ± 0.02 | 0.19 ± 0.02 | 0.21 ± 0.02 |
| Pancreas weight | 0.17 ± 0.05 | 0.23 ± 0.04* | 0.27 ± 0.04 | 0.24 ± 0.34 |
| Serum Triglyceride | 1.48 ± 0.3 | 2.02 ± 0.65* | 1.3 ± 0.17 | 1.36 ± 0.38 |
| Serum Cholesterol | 2.48 ± 0.22 | 2.58 ± 0.25 | 3.07 ± 0.44 | 3.42 ± 0.7 |
| Serum glucose | 6.61 ± 1.08 | 7.82 ± 1.75 | 29.17 ± 10.5 | 30.35 ± 7 |
| Serum Insulin | 2.7 ± 0.22 | 3.87 ± 1.05 | 7.706 ± 1.41 | 5.24 ± 2.82 |
| Serum glucagon | 282 ± 23 | 242.6 ± 18 | 248 ± 36 | 193 ± 16 |

*$P < 0.5$.

Experiment No. 3: A Human Study

At the time of beginning the *Rauvolfia-Citrus* treatment, "A" was a 72-year old male. He was diagnosed Type II diabetic following vision disturbance about 9 years prior, i.e. when he was about 63 years old. He was placed on a daily dose of 3 tablets of glibenese, as well as a medication for high blood pressure. He weighed 91 kg, registered HbA1c 8.9 (ref 4.2-6.3), C-peptide 1.89 nmol/l (ref 0.15-1.10) and non-fast blood glucose at 13.7%.

Figure 10:
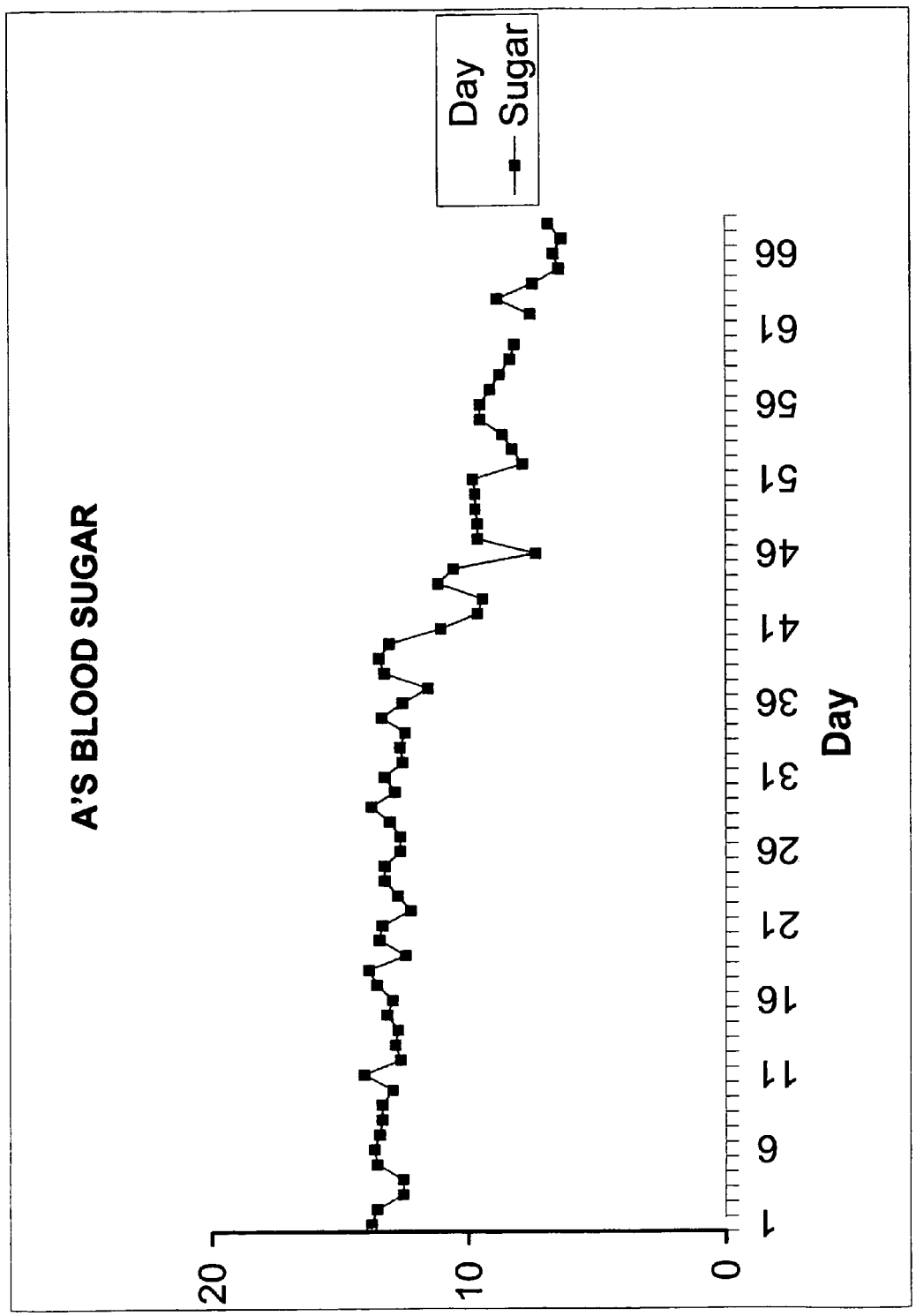
FIG. 10 shows the progression in blood sugar levels of a human case study expressed as a function of treatment period.

The patient was not satisfied with the anti-diabetes medication he was taking as he felt lethargic and often weak and tired. A also had difficulty with maintaining his weight. He stopped glibenese 3 days before commencement of the treatment and took 750 ml (i.e. 3 ordinary drinking glasses) of the *Rauvolfia-Citrus* infusion everyday for 4 months. He ate healthily, avoiding foods rich in fats, sugar and alcohol. He monitored his blood sugar and blood pressure daily. Attached FIG. 10 shows the progression in blood sugar levels of A during the treatment period.

By the end of the first 2 weeks of taking the medicine, he increased his level of exercise from 2 walks a day in the park with the dog, to the 2 walks and a 3 km trot in the park. He reported a feeling of well-being, better sight and the disappearance of several nodules on his veins. He started to loose weight and at the end of the treatment weighed 78 kg. His doctor permitted him to go off the blood pressure medication after 2 months into the *Rauvolfia-Citrus* treatment. He enjoyed a good winter 2002 through to summer 2003, a year after taking and stopping the medication. He has continued to exercise and maintain a healthy diet and abstained from drinking more than the occasional glass or two of wine. However, there was a slight drawback as he registered some hyperglycaemia in the first 2 weeks of September 2003. He blamed the lapse on the many social engagements during the summer holidays. He took a two-week treatment of the *Rauvolfia-Citrus* extract in November 2003. He subsequently stabilized at 75 kg, takes one tablet of glibenese a day, when required and at 75, still does the daily 3 km trots and walks with the dog daily.

The above results show that the medication has "curative" anti-diabetic effect if taken in combination with exercise and calorie restriction. However, there is a chance of relapse of the Type II diabetes if the patient does not continue to practice a healthy life-style.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

| Mouse Eye TOTAL-GC | Treated1 korrigeret % | Treated2 korrigeret % | Treated3 korrigeret % | Treated4 korrigeret % | Treated5 korrigeret % | Treated6 korrigeret % | Treated7 korrigeret % | Treated8 korrigeret % | Treated9 korrigeret % | Treated10 korrigeret % |
|---|---|---|---|---|---|---|---|---|---|---|
| C15:0(intern std)PC | | | | | | | | | | |
| C10:0 | 0.00 | 0.00 | 0.00 | 0.00 | 0.00 | 0.00 | 0.00 | 0.00 | 0.00 | 0.00 |
| C12:0 | 0.00 | 0.00 | 0.14 | 0.00 | 0.19 | 0.10 | 0.10 | 0.15 | 0.23 | 0.10 |
| C14:0 | 0.85 | 1.00 | 0.96 | 0.56 | 1.10 | 0.93 | 0.78 | 1.03 | 1.12 | 0.94 |
| C14:1 | 0.00 | 0.00 | 0.00 | 0.00 | 0.08 | 0.00 | 0.00 | 0.00 | 0.00 | 0.00 |
| ALD ?ret.t. | 0.00 | 0.00 | 0.00 | 0.00 | 0.00 | 0.00 | 0.00 | 0.00 | 0.00 | 0.00 |
| ALD ?ret.t. | 0.00 | 0.00 | 0.00 | 0.00 | 0.00 | 0.00 | 0.00 | 0.00 | 0.00 | 0.00 |
| C16:0 | 19.62 | 20.58 | 19.37 | 20.05 | 20.27 | 19.60 | 18.93 | 19.97 | 20.43 | 19.50 |
| C16:1n-9 | 0.47 | 0.47 | 0.50 | 0.56 | 0.55 | 0.57 | 0.47 | 0.51 | 0.46 | 0.50 |
| C16:1n-7 | 3.15 | 2.25 | 2.76 | 2.61 | 3.77 | 2.88 | 2.13 | 3.18 | 2.14 | 2.52 |

-continued

| Mouse Eye TOTAL-GC | Treated1 korrigeret % | Treated2 korrigeret % | Treated3 korrigeret % | Treated4 korrigeret % | Treated5 korrigeret % | Treated6 korrigeret % | Treated7 korrigeret % | Treated8 korrigeret % | Treated9 korrigeret % | Treated10 korrigeret % |
|---|---|---|---|---|---|---|---|---|---|---|
| C17:0 | 0.15 | 0.17 | 0.16 | 0.23 | 0.16 | 0.17 | 0.16 | 0.15 | 0.17 | 0.17 |
| C17:1 | 0.09 | 0.00 | 0.00 | 0.00 | 0.15 | 0.00 | 0.00 | 0.00 | 0.00 | 0.00 |
| C18:0 + aldehyd | 14.24 | 17.62 | 16.49 | 15.00 | 12.84 | 16.57 | 18.06 | 15.86 | 17.74 | 17.03 |
| C18:1t | 0.00 | 0.00 | 0.00 | 0.00 | 0.00 | 0.00 | 0.00 | 0.00 | 0.00 | 0.00 |
| C18:1n-9 | 19.97 | 15.74 | 17.18 | 21.06 | 21.05 | 16.48 | 15.60 | 16.19 | 15.28 | 16.38 |
| C18:1n-7 | 2.51 | 2.62 | 2.74 | 3.08 | 2.59 | 2.75 | 2.63 | 2.53 | 2.48 | 2.64 |
| pos.iso.C18:1cis | 0.52 | 0.69 | 0.71 | 0.64 | 0.44 | 0.72 | 0.81 | 0.50 | 0.58 | 0.69 |
| pos.iso.C18:1cis | 0.67 | 0.87 | 0.90 | 0.86 | 0.52 | 0.90 | 1.07 | 0.64 | 0.71 | 0.88 |
| C18:2n-6 | 13.30 | 7.25 | 8.62 | 9.40 | 14.72 | 8.38 | 7.77 | 10.76 | 7.76 | 8.69 |
| C20:0 + 18:3n-6 | 0.27 | 0.29 | 0.30 | 0.25 | 0.21 | 0.30 | 0.34 | 0.19 | 0.26 | 0.28 |
| C18:3n-6 | 0.00 | 0.00 | 0.00 | 0.00 | 0.00 | 0.00 | 0.00 | 0.00 | 0.00 | 0.00 |
| C18:3n-3 | 0.27 | 0.00 | 0.16 | 0.00 | 0.21 | 0.16 | 0.00 | 0.17 | 0.00 | 0.16 |
| C20:1(n-9) | 0.62 | 0.44 | 0.70 | 0.33 | 0.33 | 0.67 | 0.96 | 0.30 | 0.42 | 0.72 |
| C20:1(n-7)? | 0.15 | 0.16 | 0.19 | 0.00 | 0.00 | 0.18 | 0.21 | 0.00 | 0.17 | 0.19 |
| C18:4 | 0.00 | 0.00 | 0.00 | 0.00 | 0.00 | 0.00 | 0.00 | 0.00 | 0.00 | 0.00 |
| C20:2n-6 | 0.42 | 0.50 | 0.43 | 0.32 | 0.42 | 0.44 | 0.50 | 0.48 | 0.52 | 0.47 |
| C20:3n-9 | 0.19 | 0.23 | 0.27 | 0.31 | 0.17 | 0.25 | 0.27 | 0.17 | 0.20 | 0.21 |
| C20:3n-6 | 0.36 | 0.44 | 0.47 | 0.39 | 0.31 | 0.45 | 0.49 | 0.39 | 0.39 | 0.46 |
| C20:4n-6 | 6.11 | 8.55 | 7.73 | 6.94 | 5.73 | 7.83 | 8.04 | 7.22 | 8.17 | 7.75 |
| C20:4n-3? | 0.00 | 0.00 | 0.00 | 0.00 | 0.00 | 0.00 | 0.00 | 0.00 | 0.00 | 0.00 |
| C20:5n-3 | 0.00 | 0.00 | 0.00 | 0.00 | 0.00 | 0.00 | 0.00 | 0.00 | 0.00 | 0.00 |
| C24:0 | 0.00 | 0.00 | 0.00 | 0.00 | 0.00 | 0.00 | 0.00 | 0.00 | 0.00 | 0.00 |
| C22:4n-6/C24:1 | 1.07 | 1.27 | 1.31 | 0.85 | 0.84 | 1.32 | 1.73 | 1.02 | 1.18 | 1.30 |
| C22:5(n-6) | 0.00 | 0.00 | 0.00 | 0.00 | 0.20 | 0.00 | 0.21 | 0.22 | 0.26 | 0.20 |
| C22:4n-3? | 0.00 | 0.00 | 0.00 | 0.00 | 0.00 | 0.00 | 0.00 | 0.00 | 0.00 | 0.00 |
| C22:5n-3 | 0.56 | 0.71 | 0.70 | 0.68 | 0.46 | 0.73 | 0.76 | 0.64 | 0.67 | 0.70 |
| ret.t. | 0.00 | 0.00 | 0.00 | 0.00 | 0.00 | 0.00 | 0.00 | 0.00 | 0.00 | 0.00 |
| C22:6n-3 | 13.97 | 18.05 | 16.94 | 15.78 | 12.31 | 17.34 | 17.70 | 17.57 | 18.47 | 17.30 |
| sum % | 99.55 | 99.92 | 99.27 | 99.27 | 99.61 | 99.72 | 99.73 | 99.84 | 99.83 | 99.77 |
| ug ident. Fatty acid-int. std | 515.64 | 290.52 | 343.29 | 331.90 | 366.79 | 354.43 | 405.76 | 341.50 | 302.07 | 379.70 |
| Weight of eye in mg. | 30.54 | 36.97 | 36.96 | 33.46 | 29.25 | 40.40 | 43.19 | 35.00 | 37.55 | 35.48 |
| ug ident. Fatty acid(as PC)pr. mg tissue | 16.88 | 7.86 | 9.29 | 9.92 | 13.22 | 8.77 | 9.39 | 9.76 | 8.04 | 10.70 |
| Linoleic acid (as PC) pr. mg tissue | 2.25 | 0.57 | 0.80 | 0.93 | 1.95 | 0.74 | 0.73 | 1.05 | 0.62 | 0.93 |
| Arachidonic acid (as PC) pr. mg tissue | 1.03 | 0.67 | 0.72 | 0.69 | 0.76 | 0.69 | 0.76 | 0.70 | 0.66 | 0.83 |
| Arachidonic:Linoleic acid ratio | 0.46 | 1.18 | 0.90 | 0.74 | 0.39 | 0.93 | 1.03 | 0.67 | 1.05 | 0.89 |
| Linolenic acid (as PC) pr. mg tissue | 0.05 | 0.00 | 0.01 | 0.00 | 0.03 | 0.01 | 0.00 | 0.02 | 0.00 | 0.02 |
| DHAC (as PC) pr. mg tissue | 2.36 | 1.42 | 1.57 | 1.57 | 1.63 | 1.52 | 1.66 | 1.72 | 1.48 | 1.85 |
| DHAC:Linolenic acid ratio | 51.12 | #DIV/0! | 106.1429 | #DIV/0! | 57.63158 | 109.0714 | #DIV/0! | 102.6667 | #DIV/0! | 109.6429 |
| Stearoyl CoA desaturase activity | 1.58 | 1.04 | 1.21 | 1.61 | 1.84 | 1.16 | 1.01 | 1.18 | 1.00 | 1.12 |
| Sum of MUFA | 3.90 | 1.48 | 1.91 | 2.43 | 3.17 | 1.75 | 1.80 | 1.86 | 1.46 | 2.11 |
| Sum of PUFA | 5.94 | 2.81 | 3.28 | 3.35 | 4.57 | 3.12 | 3.36 | 3.67 | 2.93 | 3.85 |
| Sum of saturated FA (treated) | 5.72 | 3.00 (M49:V49) | 3.33 | 3.48 | 4.38 | 3.17 | 3.47 | 3.50 | 3.07 | 3.91 |

The invention claimed is:

1. A biologically active composition for lowering tissue fatty acid content and blood glucose levels consisting essentially of a concentrated extract obtained from multiple extractions of the dried leaves and stems of *Rauvolfia vomitoria* and the whole fruits of *Citrus aurantium*.

2. The composition of claim 1, wherein the extract is separated from the dried leaves and young stems of *Rauvolfia vomitoria* and the whole fruits of *Citrus aurantium*.

3. The composition of claim 1 or 2, further comprising a carrier.

4. A biologically active composition for lowering tissue fatty acid content and blood glucose levels consisting essentially of a concentrated extract obtained from multiple extractions of the dried leaves and young stems of *Rauvolfia vomitoria*, the whole fruits of *Citrus aurantium* and an effective amount of an agent other than the extract, that lowers tissue fatty acid content and lowers blood glucose levels.

5. A kit for treating or ameliorating the symptoms of a disorder associated with abnormally elevated levels of blood glucose in a subject comprising a therapeutically effective amount of the composition of claim 3, and instructions for use.

6. The kit of claim 5, wherein the disorder is selected from the group consisting of abnormally elevated levels blood glucose in a subject are selected from the group consisting of diabetes Type II, abnormal stearoyl-CoA desaturase activity, hyperphagia, abnormal lipid mobilization, abnormal fatty acid profile from the eye of the subject, ulcers and a glucosuria.

7. The composition of any of claim 3, wherein the composition comprises an effective amount of the extract to reduce elevated tissue fatty acid content when administered to a subject in need thereof.

8. The composition of claim 3, wherein the composition comprises an effective amount of the extract to reduce abnormally elevated blood glucose levels when administered to a subject in need thereof.

9. The composition of claim 1 or 2, wherein the extract is concentrated by multiple extractions of a boiled composition consisting essentially of the dried leaves and young stems of *Rauvolfia vomitoria* and the whole fruits of *Citrus aurantium* and freeze drying the boiled composition.

10. The composition of claim 1 or 2, wherein the extract is concentrated by multiple extractions of a boiled composition consisting essentially of about 400 g total weight of the dried leaves and young stems of *Rauvolfia vomitoria* and about 2 kg total weight of whole fruit of *Citrus aurantium* and about 8 liters of carrier.

11. A pharmaceutical composition comprising the composition of claim 4 and a carrier.

* * * * *

UNITED STATES PATENT AND TRADEMARK OFFICE
CERTIFICATE OF CORRECTION

Figure 9:
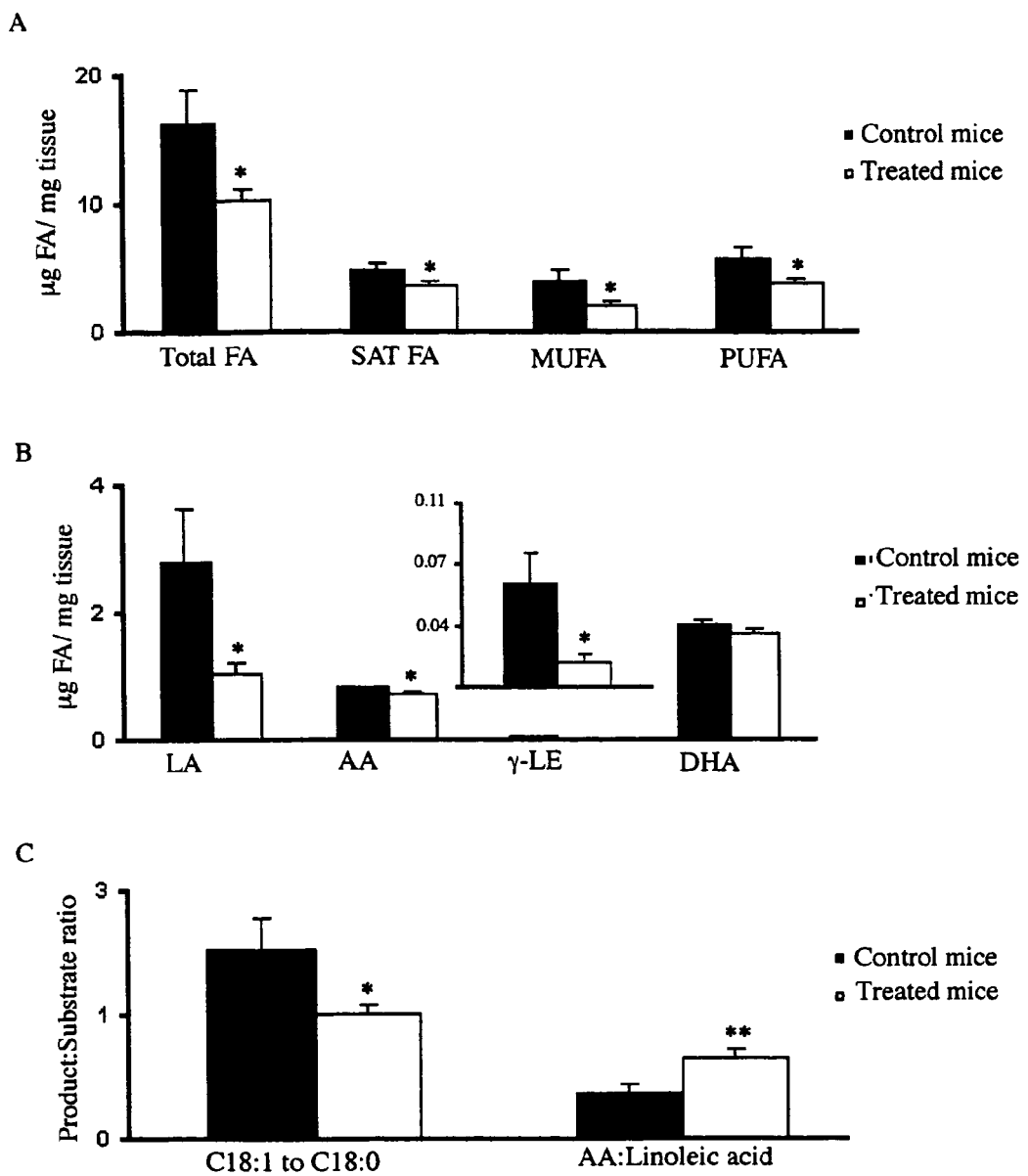
FIG. 9 shows the effect of the *Rauvolfia-Citrus* extract treatment on (A) Fatty acid content; (B) Essential fatty acid content and (C) Estimated Stearoyl-CoA and delta6 desaturase activities in the eye of control (n=9) and treated (n=10) bred diabetic C57BL/KsBom-db mice after the 6 week treatment period. Data are expressed as mean±SEM values. Significant difference of data from treated mice to that in the untreated controls is expressed as *=P<0.05; **=P<0.01.

PATENT NO. : 7,429,395 B2 Page 1 of 1
APPLICATION NO. : 11/260504
DATED : September 30, 2008
INVENTOR(S) : Joan Campbell-Tofte It is certified that error appears in the above-identified patent and that said Letters Patent is hereby corrected as shown below:

In column 19, line 42, please replace "FIG. 10A" with -- FIG. 9A --

In column 19, line 61, please replace "protien" with -- protein --

In the table immediately preceding the claims, please add the heading -- Appendix I --

Signed and Sealed this

Sixteenth Day of December, 2008

JON W. DUDAS
*Director of the United States Patent and Trademark Office*